US009547013B2

(12) United States Patent
Cezar et al.

(10) Patent No.: US 9,547,013 B2
(45) Date of Patent: Jan. 17, 2017

(54) MOLECULE BIOMARKERS OF AUTISM

(75) Inventors: Gabriela Gebrin Cezar, Middleton, WI (US); Alan M. Smith, Madison, WI (US)

(73) Assignees: Wisconsin Alumni Research Foundation, Madison, WI (US); Stemina Biomarker Discovery, Inc., Madison, WI (US)

( * ) Notice: Subject to any disclaimer, the term of this patent is extended or adjusted under 35 U.S.C. 154(b) by 0 days.

(21) Appl. No.: 13/098,249

(22) Filed: Apr. 29, 2011

(65) Prior Publication Data

US 2012/0190055 A1    Jul. 26, 2012

Related U.S. Application Data

(60) Provisional application No. 61/329,515, filed on Apr. 29, 2010.

(51) Int. Cl.
| | | |
|---|---|---|
| *G01N 30/00* | (2006.01) | |
| *C12Q 1/02* | (2006.01) | |
| *B01D 59/44* | (2006.01) | |
| *G01N 33/68* | (2006.01) | |
| *G01N 33/92* | (2006.01) | |
| *G01N 33/94* | (2006.01) | |

(52) U.S. Cl.
CPC .......... *G01N 33/6896* (2013.01); *G01N 33/92* (2013.01); *G01N 33/94* (2013.01); *G01N 2800/28* (2013.01)

(58) Field of Classification Search
CPC .... G01N 33/6896; G01N 33/94; G01N 33/92; G01N 2800/28; G01N 27/62; G01N 30/00; H01J 49/26; H01J 49/40
USPC ............................ 435/29; 73/61.52; 250/282
See application file for complete search history.

(56) References Cited

U.S. PATENT DOCUMENTS 5,686,311 A * 11/1997 Shaw ............................. 436/86
8,273,575 B2   9/2012 Goodenowe

FOREIGN PATENT DOCUMENTS

| WO | 2004059293 | 2/2004 |
| WO | 2006090185 | 8/2006 |
| WO | 2006121952 | 11/2006 |
| WO | 2008021515 | 1/2008 |
| WO | 2009151967 | 12/2009 |

OTHER PUBLICATIONS

Aldred et al. Plasma Amino Acid Levels in Children With Autism and Their Families; Journal of Autism and Developmental Disorders, vol. 33, No. 1 (2003) pp. 93-97.*
Armstrong et al. Analysis of 25 Underivatized Amino Acids in Human Plasma Using Ion-Pairing Reversed-Phase Liquid Chromatography/Time-of-Flight Mass Spectrometry; Rapid Communications in Mass Spectrometry, vol. 21 (2007) pp. 2717-2726.*
Jauniaux et al. Free Amino Acids in Human Fetal Liver and Fluids at 12-17 Weeks of Gestation; Human Reproduction, vol. 14, No. 6 (1999) pp. 1638-1641.*
James et al. Metabolic Biomarkers of Increased Oxidative Stress and Impaired Methylation Capacity in Children With Autism; American Journal of Clinical Nutrition, vol. 80 (2004) pp. 1611-1617.*
Kale et al. Elevated Amniotic Fluid Amino Acid Levels in Fetuses With Gastroschisis; Brazilian Journal of Medical and Biological Research, vol. 39 (2006) pp. 1021-1025.*
Anonymous. Considerations for Selecting GC/MS or LC/MS for Metabolomics; Agilent Technologies (2007) downloaded from www.chem.agilent.com/Library/selectionguide/Public/5989-6328EN.pdf on Apr. 3, 2015.*
Baggot et al. Organic Acid Concentrations in Amniotic Fluid Found in Normal and Down Syndrome Pregnancies; Fetal Diagnosis and Therapy, vol. 23 (2008) pp. 245-248.*
Jurecka et al. Clinical, Biochemical, and Molecular Finding in Seven Polish Patients With Adenylosuccinate Lyase Deficiency; Molecular Genetics and Metabolism, vol. 94 (2008) pp. 435-442.*
Kershenobich et al. Relationship Between Blood Lactic and Serum Proline in Alcoholic Liver Cirrhosis; Gastroenterology, vol. 80 (1981) pp. 1012-1015.*
Mochel et al. Elevated CSF N-Acetylaspartylglutamate in Patients With Free Sialic Acid Storage Diseases; Neurology, vol. 74, No. 4 (2010) pp. 302-305.*
Molina et al. Cerebrospinal Fluid Levels of Non-Neurotransmitter Amino Acids in Patients With Alzheimer's Disease; Journal of Neural Transmission, vol. 105 (1998) pp. 279-286.*
Pitt, J.J. Principles and Applications of Liquid Chromatography-Mass Spectrometry in Clinical Biochemistry; Clincal and Biochemical Reviews, vol. 30 (2009) pp. 19-34.*
Pomara et al. Glutamate and Other CSF Amino Acids in Alzheimer's Disease; The American Journal of Psychiatry, vol. 149, No. 2 (1992) pp. 251-254.*
Lander et al., "Genetic Dissection of Complex Traits," 1994, Science, 265:2037-2048.
Laurence et al., "Glial fibrillary acidic protein is elevated in superior frontal, parietal and cerebellar cortices of autistic subjects," 2005, Cerebellum, 4:206-210.
Luján et al., "Glutamate and GABA Receptor Signalling in the Developing Brain," 2005, Neuroscience, 130:567-580.
Luján et al., "Subcellular regulation of metabotropic GABA receptors in the developing cerebellum," 2007, Cerebellum, 6:123-129.
McCracken et al., "Risperidone in Children With Autism and Serious Behavioral Problems," 2002, N. Engl. J. Med., 347:314-321.
Mochel et al., 2010, "Elevated CSF N-acetylaspartylglutamate in patients with free sialic acid storage diseases," Neurology, 74:302-305.

(Continued)

*Primary Examiner* — Scott Long
*Assistant Examiner* — Paul Martin
(74) *Attorney, Agent, or Firm* — McDonnell Boehnen Hulbert & Berghoff LLP

(57) ABSTRACT

This invention provides methods and biomarkers for diagnosing autism by identifying cellular metabolites differentially produced in autistic patient samples versus non-autistic controls. Methods for identifying a unique profile of metabolites present of secreted in brain tissue, cerebrospinal fluid, plasma, or biofluids of autistic samples are described herein. The individual metabolites or a pattern of secreted metabolites provide metabolic signatures of autism, which can be used to provide a diagnosis thereof.

6 Claims, 13 Drawing Sheets

(56) References Cited

OTHER PUBLICATIONS

Moore et al., "Treating Functional Impairment of Autism with Selective Serotonin-Reuptake Inhibitors," 2004, Ann. Pharmacother., 38:1515-1519.
Moretti et al., "Cerebral folate deficiency with developmental delay, autism, and response to folinic acid," 2005, Neurology, 64:1088-1090.
Oba et al., "A Bayesian missing value estimation method for gene expression profile data," 2003, Bioinformatics, 19:2088-2096.
Pardo et al., "The Neurobiology of Autism," 2007, Brain Pathol., 17:434-447.
Parry et al., "Paper Chromatography of 56 Amino Compounds USI~G Phenol and Butanol-Acetic Acid As Solvents," 1957, Clin. Chim. Acta, 2:115-125.
Pasca et al., "High levels of homocysteine and low serum paraoxonase 1 arylesterase activity in children with autism," 2006, Life Sci., 78:2244-2248.
Pastural et al., "Novel plasma phospholipid biomarkers of autism-:Mitochondrial dysfunction as a putative causative mechanism," 2009, Prostag. Leukotr. Ess., 81:253-264.
Purcell et al., "Postmortem brain abnormalities of the glutamate neurotransmitter system in autism," 2001, Neurology, 57:1618-1628.
Quinones et al., 2009, "Metabolomics tools for identifying biomarkers for neuropsychiatric diseases," Neurobiol Dis., 35: 165-176.
Rasalam et al., "Characteristics of fetal anticonvulsant syndrome associated autistic disorder," 2005, Dev. Med. Child Neurol., 47:551-555.
Santangelo et al., "What is Known About Autism," 2005, Am. J. Pharmacogenomic., 5:71-92.
Shinohe et al., "Increased serum levels of glutamate in adult patients with autism," 2006, Prog. Neuro-Psychopha., 30:1472-1477.
Soga et al., "Differential Metabolomics Reveals Ophthalmic Acid as an Oxidative Stress Biomarker Indicating Hepatic Glutathione Consumption," 2006, J. Biol. Chem., 281:16768-78.
Smith et al., "XCMS: Processing Mass Spectrometry Data for Metabolite Profiling Using Nonlinear Peak Alignment, Matching, and Identification," 2006, Anal. Chem., 78:779-787.
Tallan et al., "L-Cystathionine in Human Brain," 1958, J. Biol. Chem., 230:707-716.
Tanaka et al., 1982, "Compilation of gas chromatographic retention indices of 163 metabolically important organic acids, and their use in detection of patients with organic acidurias," J. Chromatogr., 239:301-322.
Taniura et al., "Tex261 modulates the excitotoxic cell death induced by N-methyl-D-aspartate (NMDA) receptor activation," 2007, Biochem. Bioph. Res. Co., 362:1096-1100.
Tashiro et al., "NMDA-receptor-mediated, cell-specific integration of new neurons in adult dentate gyrus," 2006, Nature, 442:929-933.
Tautenhahn et al., "Highly sensitive feature detection for high resolution LC/MS," 2008, BMC Bioinformatics, 9:504.
Tews et al., "Atypical amino acids inhibit histidine, valine, or lysine transport into rat brain," 1983, Am. J. Physiol-Reg I., 245:556-563.
Tews et al., "Tissue Amino Acids in Rats Fed Norleucine, Norvaline, Homoarginine or Other Amino Acid Analogues," 1986, J. Nutr., 116:1464-1472.
Vargas et al., "Neuroglial Activation and Neuroinflammation in the Brain of Patients with Autism," 2005, Ann Neurol., 57:67-81.
Waage-Baudet et al., "Abnormal serotonergic development in a mouse model for the Smith-Lemli-Opitz syndrome: implications for autism," 2003, Int. J. Dev. Neurosci., 21:451-459.
Wang et al., "Genomic basis of cystathioninuria (MIM 219500) revealed by multiple mutations in cystathionine gamma-lyase (CTH)," 2003, Hum. Genet., 112:404-408.
Woods et al., "Urinary Porphyrin Excretion in Neurotypical and Autistic Children," 2010, Environ. Health Persp., 118:1450-1457.
Yap et al., "Urinary metabolic Phenotyping differentiates children with Autism for their unaffected siblings and age-matched controls," 2010, J. Proteome Res., 9:2966-3004.

Zhao et al., "Association Analysis of Serotonin Transporter Promoter Gene Polymorphism With ADHD and Related Symptomatology," 2005, Int. J. Neurosci., 115:1183-1191.
Zhao et al., "Neural Tube Defects and Maternal Biomarkers of Folate, Homocysteine, and Glutathione Metabolism," 2006, Birth Defects Res. A., 76:230-236.
Asano et al., "Autism in tuberous sclerosis complex is related to both cortical and subcortical dysfunction," 2001, Neurology, 57:1269-1277.
Baron-Cohen et al., "Sex Differences in the Brain:Implications for Explaining Autism," 2005, Science, 310:819-23.
Baslow, "The Astrocyte Surface NAAG Receptor and NAAG Peptidase Signaling Complex as a Therapeutic Target," 2008, Drug News & Perspect. 2: 251-257.
Benarroch, N-Acetylaspartate and N-acetylaspartylglutamate Neurobiology and clinical significance, 2008, Neurology, 70:1353-1357.
Betancur et al., "Serotonin transporter gene polymorphisms and hyperserotonemia in autistic disorder," 2002, Mol. Psychiatry, 7:67-71.
Blaylock et al., "Immune-Glutamatergic Dysfunction as a Central Mechanism of the Autism Spectrum Disorders," 2009, Curr. Med. Chem., 16:157-170.
Bourcier et al., 2009, "Use of diagnostic neutral losses for structural information on unknown aromatic metabolites: an experimental and theoretical study", Rapid Commun. Mass Spectrom., 23: 93-103.
Bryson et al., "Epidemiology of Autism: Prevalence, Associated Characteristics, and Implications for Research and Service Delivery," 1998, Ment. Retard. Dev. D. R., 4:97-103.
Buxbaum et al., "Linkage analysis for autism in a subset families with obsessive-compulsive behaviors: Evidence for an autism susceptibility gene on chromosome 1 and further support for susceptibility genes on chromosome 6 and 19," 2004, Mol. Psychiatry, 9:144-150.
Cezar et al., "Identification of SInaH Molecules from HIHI1an EII1bryonic Stem Cells Using Metabolomics," 2007, Stem Cells Dev., 16:869-882.
Chauhan et al., "Oxidative stress in autism," 2006, Pathophysiology, 13:171-181.
Chugani et al, "Developmental Changes in Brain Serotonin Synthesis Capacity in Autistic and Nonautistic Children," 1999, Ann. Neurol. 45:287-295.
Chugani et al., "Serotonin in Autism and Pediatric Epilepsies," 2004, Ment. Retard. Dev. D. R., 10:112-116.
Cummings et al., "Quantitative analysis of biomarkers by LC—MS/MS," 2009, J Chromatogr B., 877:1221.
Database accession No. HMDB00099, 2005, "L-Cystathionine," http://www.hmdb.ca/metabolites.
Database accession No. HMDB01067, 2005, "N-Acetylaspartylglutamic acid," http://www.hmdb.ca/metabolites/.
Database accession No. HMDB00991, 2005, "DL-2-Aminooctanoic acid," http://www.hmdb.ca/metabolites.
Database accession No. HMDB00450, 2005, "5-Hydroxylysine," http://www.hmdb.ca/metabolites.
Database accession No. HMDB00894, 2005, "Vinylacetylglycine," http://www.hmdb.ca/metabolites.
Database accession No. HMDB00564, 2005, "PC(16:0/16:0)," http://www.hmdb.ca/metabolites.
Database accession No. HMDB00797, 2005, "SAICAR," http://www.hmdb.ca/metabolites.
Database accession No. HMDB04827, 2006, "Proline betaine," http://www.hmdb.ca/metabolites.
Database accession No. HMDB06607, 2007, "3'-Sialyllactosamine," http://www.hmdb.ca/metabolites.
Database accession No. HMDB06744, 2008, "3-carboxy-1-hydroxypropylthiamine Diphosphate," http://www.hmdb.ca/metabolites.
Database accession No. HMDB12153, 2009, "3,4-Dihydroxybenzylamine," http://www.hmdb.ca/metabolites.
Deth et al., "How environmental and genetic factors combine to cause autism: A redox/methylation hypothesis," 2008, Neurotoxicology, 29:190-201.

(56) References Cited

OTHER PUBLICATIONS

Dettmer et al., "Mass Spectrometry-Based Metabolomics," 2007, Mass Spectrom. Rev. 26:51-78.
De Bree et al., "Diagnosis of inherited adenylosuccinase deficiency by thin-layer chromatography of urinary imidazoles and by automated cation exchange column chromatography of purines," 1986, Clin. Chim. Acta., 156:279-287.
De Vera et al., "Spermine Induces Cell Death in Cultured Human Embryonic Cerebral Cortical Neurons Through N-Methyl-D-Aspartate Receptor Activation," 2008, J Neurosci Res., 86:861-872.
Devlin et al., "Autism and the serotonin transporter: the long and short of it," 2005, Mol. Psychiatr., 10:1110-1116.
Dikranian et al., "Apoptosis in the in Vivo Mammalian Forebrain," 2001, Neurobiol Dis. 8:359-379.
Du et al., "Improved peak detection in mass spectrum by incorporating continuous wavelet transform-based pattern matching," 2006, Bioinformatics, 22:2059-2065.
Evans et al., "Altered amino acid excretion in children with autism," 2008, Nutr. Neurosci., 11:9-17.
Fatemi et al., "Glutamic Acid Decarboxylase 65 and 67 kDa Proteins are Reduced in Autistic Parietal and Cerebellar Cortices," 2002, Biol. Psychiat., 52:805-810.
Folstein et al., "Genetics of Autism: Complex Aetiology for a Heterogeneous Disorder," 2001, Nat. Rev. Genet., 2:943-955.
Friedman et al., "Gray and White Matter Brain Chemistry in Young Children With Autism," 2006, Arch. Gen. Psychiatry, 63:786-794.
Geier et al., "A Prospective Study of Transsulfuration Biomarkers in Autistic Disorders," 2009, Neurochem. Res. 34:386-393.
Glish et al., "The Basics of Mass Spectrometry in the Twenty-First Century," 2003, Nat. Rev. Drug Discov., 2:140-150.
Guillemin et al., "Kynurenine pathway metabolism in human astrocytes: a paradox for neuronal protection," 2001, J Neurochem., 78:842-853.
Heaton et al., "Amelioration of Ethanol-Induced Neurotoxicity in the Neonatal Rat Central Nervous System by Antioxidant Therapy," 2000, Alcohol. Clin. Exp. Res., 24:512-518.
Jaeken et al., 1984, "An infantile autistic syndrome characterised by the presence of succinylpurines in body fluids," The Lancet, 2: 1058-1061.
James et al., "Metabolic biomarkers of increased oxidative stress and impaired methylation capacity in children with autism," 2004, Am. J. Clin. Nutr., 80:1611-1617.
James et al., "Metabolic Endophenotype and Related Genotypes are Associated With Oxidative Stress in Children With Autism," 2006, Am. J. Med. Genet. B., 141B:947-956.
James et al., "Efficacy of methylcobalamin and folinic acid treatment on glutathione redox status in children with autism," 2009, Am. J. Clin. Nutr., 89:425-430.
James et al., 2010, "A functional polymorphism in the reduced folate carrier gene and DNA hypomethylation in mothers of children with autism," Am. J. Med. Genet. B., 153B:1209-1220.
Kemper et al., "Neuropathology of Infantile Autism," 1998, J. Neuropathol. Exp. Neur., 57:645-652.
Kern, "Purkinje cell vulnerability and autism: a possible etiological connection," 2003, Brain Dev., 25:377-382.
Kim et al., "Altered serotonin synthesis, turnover and dynamic regulation in multiple brain regions of mice lacking the serotonin transporter," 2005, Neuropharmacology, 49:798-810.
Kleinhans et al., "N-acetyl aspartate in autism spectrum disorders: Regional effects and relationship to fMRI activation," 2007, Brain Res., 1162:85-97.
Knöpfel et al., "Metabotropic glutamate receptors in the cerebellum with a focus on their function in Purkinje cells," 2002, Cerebellum, 1:19-26.

\* cited by examiner

MOLECULE BIOMARKERS OF AUTISM

This application claims the priority benefit of U.S. provisional patent application Ser. No. 61/329,515 filed Apr. 29, 2010, the entirety of which is herein incorporated by reference.

FIELD OF THE INVENTION

This invention relates to autism and diagnosing autism and autism spectrum disorders. Specifically, the invention provides methods and biomarkers for identifying individuals, particularly children, having autism and autism spectrum disorders. More particularly, the invention provides methods for identifying metabolites secreted by brain tissues and into biofluids of individuals with autism, wherein such metabolites have a molecular weight from about 10 Daltons to about 1500 Daltons. The invention provides multiple collections or spectra that comprise one or a plurality of such metabolites that are present in autistic individuals that are diagnostically and significantly different from levels found in non-autistic individuals. Collections of one or more differentially secreted metabolites provided herein comprise metabolic signatures diagnostic for autism. Additionally, specific biomarkers for autism are identified herein.

BACKGROUND OF THE INVENTION

Autism is a neurological disorder characterized by alterations in social interaction, language development, repetitive movements and patterns of behavior. Its prevalence has increased from 1 in 2,325 births prior to the 1980's to an alarming 1 in 101 births today (Blaylock et al., 2009, Curr. Med. Chem. 16:157-170). Autism is a very complex neurological disorder that does not follow strictly genetic or deterministic etiology (Lander et al., 1994, Science, 265: 2037-48; Baron-Cohen et al., 2005, Science, 310:819-23; Santangelo et al., 2005, Am. J. Pharmacogenomic. 5:71-92). Accordingly, defining a role for metabolism in the pathogenesis of autism is important to developing an understanding of the disorder and providing an accurate diagnosis and patient management of the disease, because strictly genetic causes account for only approximately 10% of autism cases. Multiple candidate susceptibility genes have been identified, such as the serotonin transporter gene (5HTT), the GABA receptor β subunit (GABRB3), ubiquitin ligase 3 (UBE3A), wingless type MMTV integration site family member 2 (WNT2), and reelin (RELN) (Folstein et al., 2001, Nat. Rev. Genet. 2:943-955; Buxbaum et al., 2004, Mol. Psychiatry, 9:144-150; Devlin et al., 2005, Mol. Psych. 10:1110-1116). Despite the genetic diversity underlying mutations and patient symptoms (McCracken et al., 2002, N. Engl. J. Med. 347:314-321; Moore et al., 2004, Ann. Pharmacother. 38:1515-1519; Zhao et al., 2005, Intern. J. Neuroscience, 115:1183-1191) there seems to be a converging metabolic dysfunction across cases (Bryson et al., 1998, Mental Retard. Dev. Disabil. Res. Rev. 4:97-103; Betancur et al., 2002, Mol. Psychiatry, 7:67-71; Moore et al., 2004, Ann. Pharmacotherapy. 38:1515-19). Metabolism and metabolic alterations can play a significant role during neurodevelopment and autism pathogenesis (Pardo et al., 2007, Brain Pathol. 17:434-447). Thus, comparative studies to examine global biochemical differences between autistic and non-autistic brain can identify specific metabolic pathways that contribute to autism onset and progress. (Moore et al., 2004, Pharmacother. 38:1515-1519; Rasalam et al., 2005, Dev. Med. Child Neurol. 47 (8):551-555).

SUMMARY OF THE INVENTION

This invention provides reagents and methods for identifying a plurality of metabolite compounds differentially produced in autistic patients, as well as methods for using one or a plurality of such identified metabolite compounds for providing a diagnosis of autism or autistic spectrum disorder. Said metabolites are found using the methods set forth herein differentially secreted in patient tissues or biofluids, particularly brain-associated biofluids such as cerebrospinal fluid. These metabolites are found in either greater or lesser amounts in autistic as compared to non-autistic individuals. Additionally, the invention provides biomarkers, either individually or in collections of spectra of a plurality of said biomarkers, comprising the metabolites differentially detected in biofluids from autistic individuals, particularly children. Said collections or spectra are useful in the practice of the methods of the invention for diagnosing of autism.

As set forth herein, multiple neurodevelopmental disorders including autism can produce alterations in common metabolic pathways. It will be understood by those skilled in the art that metabolites (e.g., small molecules from about 10 Daltons to about 1500 Daltons) present in autistic samples versus controls can be detected at varying relative levels, which provides information regarding the biochemical spectrum of compounds present in both diseased and healthy tissue. Such spectra provide "biochemical fingerprints" comprising combinations of metabolites whose changes, together, can serve as specific indicators of autism. As shown herein, certain metabolites, including those involved in glutamate, cysteine, methionine and γ-amino butyric acid (GABA) metabolism can have a synergistic role on the cerebellar pathogenesis of autism. Additionally, non-annotated or unreported metabolites were found to be present in autistic brains in a statistically-significant manner and also provide useful candidate biomarkers for autism and autism spectrum disorders. Metabolites identified herein provide sensitive and unique biochemical signatures of autism that are useful as diagnostic biomarkers for the disorder.

This disclosure herein of these metabolic signatures of autism and autistic spectrum disorders is the first to apply metabolomics on postmortem autistic brains and to provide a fingerprint of metabolites and their changes, between autistic and non-autistic individuals. The studies provided herein identified metabolites that were significantly altered in the brains of autistic subjects as compared to non-autistic controls. In addition, subsets of metabolites that were commonly altered in autistic tissues were identified. As set forth in more detail below, differentially-secreted metabolites having a molecular weight from between about 10 Daltons to about 1500 Daltons were identified by liquid chromatography electrospray ionization time-of-flight mass spectroscopy (LC-ESI-TOF-MS) and/or hydrophilic interaction chromatography (HILIC), although the skilled worker will recognize that these methods are non-limiting and that other methods for detecting metabolites in biofluids from autistic patients can be utilized in the practice of the methods of this invention. However, the skilled worker will also recognize that this modality of mass spectrometry as applied to metabolomic analysis of fresh frozen brain tissue was highly sensitive (e.g., resolution of 3 ppm) and capable of detecting metabolites at very low abundances (i.e., micromolar to picomolar concentrations). In addition, other analytical chemistry platforms known in the art for practicing metabolomic methods, such as nuclear magnetic resonance (NMR) are less sensitive than mass spectrometry, requiring larger amounts of biological samples to detect metabolites at significantly higher concentrations (reviewed in Glish et al., 2003, *Nat. Rev. Drug Discov.* 2:140-150); nevertheless, the invention expressly envisions using such methods, and other methods known in the art, under appropriate circumstances.

Specific embodiments of this invention will become evident from the following more detailed description of certain preferred embodiments and the claims.

BRIEF DESCRIPTION OF THE DRAWINGS

These and other objects and features of this invention will be better understood from the following detailed description taken in conjunction with the drawings, wherein: FIG. 1 (A) represents HILIC chromatography and FIG. 1 (B) represents C18 chromatography. Autistic samples are designated by dashed lines and non-autistic controls are designated by black lines.

FIG. 3 (A) shows the results of metabolomics analysis of fresh frozen postmortem brain samples of autistic (dashed lines) and non-autistic controls (black lines) showing a significant increase in the abundance of L-cystathionine (exact mass 222.0628) in the post vermis and lateral hemispheres of autistic brains. FIG. 3 (B) shows EIC having the retention time of a chemical standard. FIG. 3 (C) shows EIC of brain samples run at the same time as chemical standard, which matched retention time of chemical standard shown in FIG. 3 (B). FIG. 3 (D) is a mean plot of the abundance of L-cystathionine in autistic and control brain samples. An ANOVA on the difference of the means was statistically significant ($p=0.019$). Error bars are standard error of the mean.

FIG. 5 (A) shows the results 20 of metabolomic analysis of fresh frozen postmortem brain samples of autistic (dashed lines) and non-autistic controls (black lines), revealing a significant decrease in the abundance of 2-aminooctanoic acid (exact mass 159.1253) in the post vermis and lateral hemispheres of autistic brains, as shown by extracted ion chromatograms (EICs). FIG. 5 (B) is an EIC showing the retention time of a chemical standard. FIG. 5 (C) are EICs of brain samples run at same time as chemical standard, which match retention time of control shown in FIG. 5 (B). FIG. 5 (D) is a mean plot of the abundance of 2-aminooctanoic acid in autistic and control brain samples. An ANOVA on the difference of the means was statistically significant ($p=0.027$). Error bars are standard error of the mean.

FIG. 6 (A) shows the results of metabolomic analysis of fresh frozen postmortem brain samples of autistic (dashed) and non-autistic controls (black lines) of N-acetylaspartylglutamic acid (exact mass 304.0909) in the post vermis and lateral hemispheres. FIG. 6 (B) is an EIC showing retention times of chemical standards. FIG. 6 (C) are EICs of brain samples run at the same time as the chemical standard, which matched retention time shown in FIG. 6 (B). FIG. 6 (D) is a mean plot of the abundance of N-acetylaspartylglutamic acid in autistic and control brain samples. An ANOVA on the difference of the means was not statistically significant at p less than 0.05 ($p=0.054$), but was at a p-value less than 0.1. Error bars are standard error of the mean.

DETAILED DESCRIPTION OF THE PREFERRED EMBODIMENTS

Figure 1A:
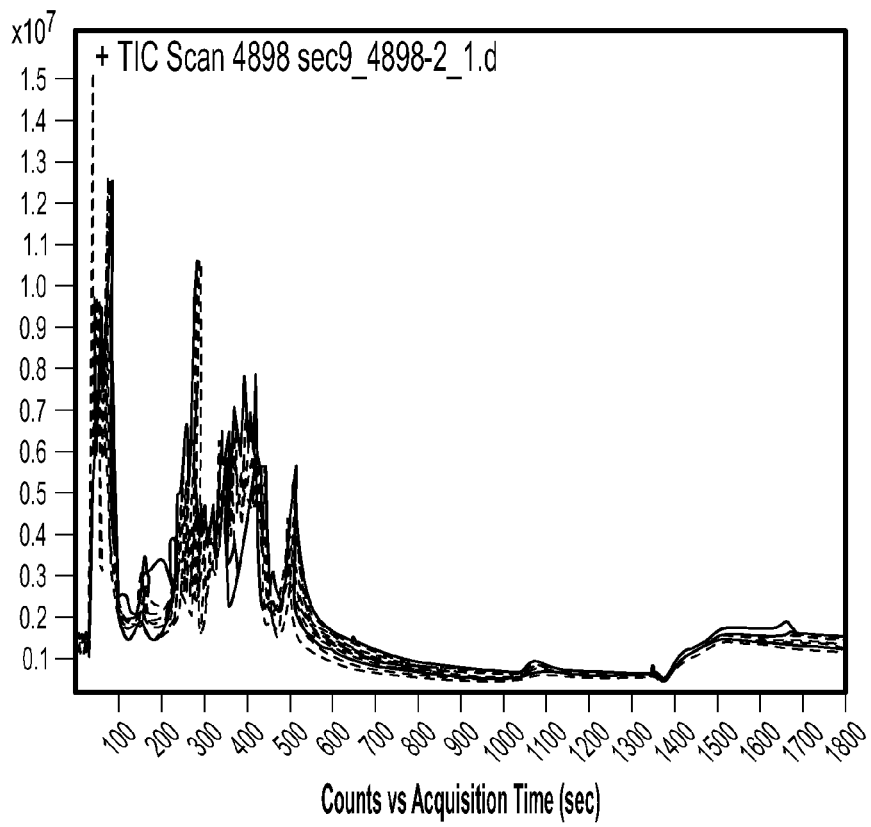
FIGS. 1 (A) and (B) are total ion chromatograms of all postmortem brain samples.
Figure 1A:
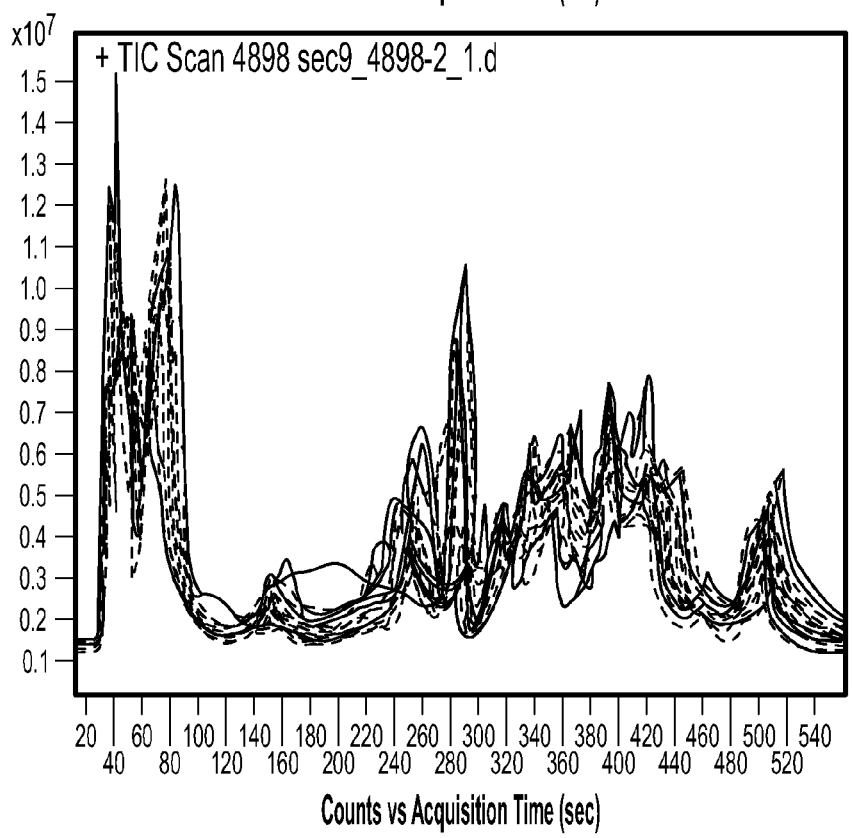
Figure 1B:
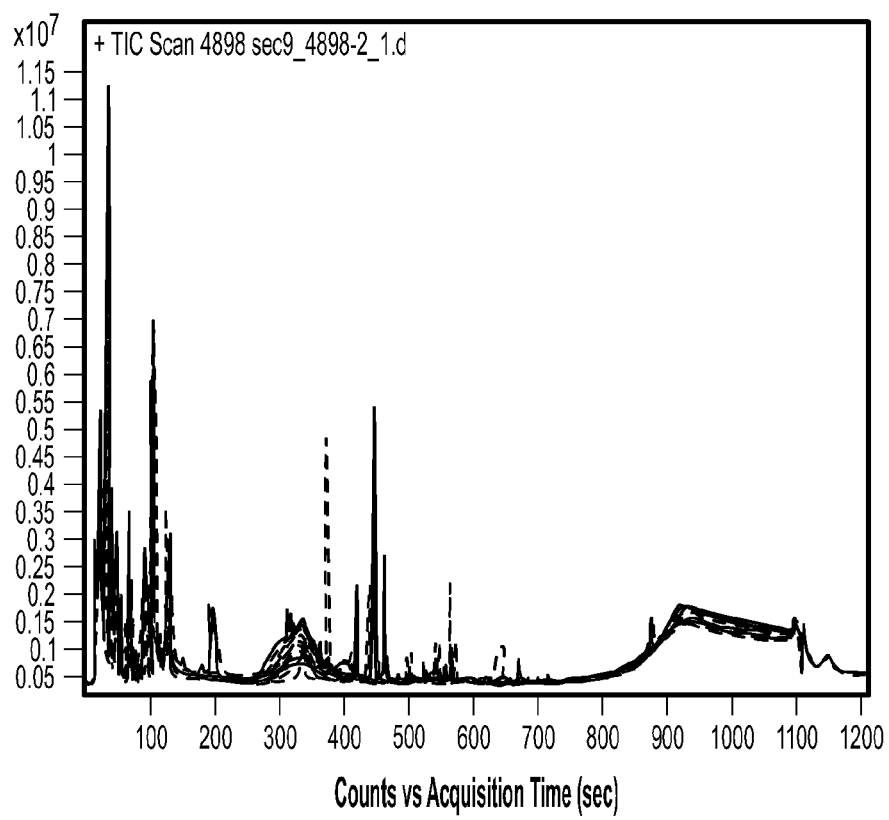
Figure 1B:
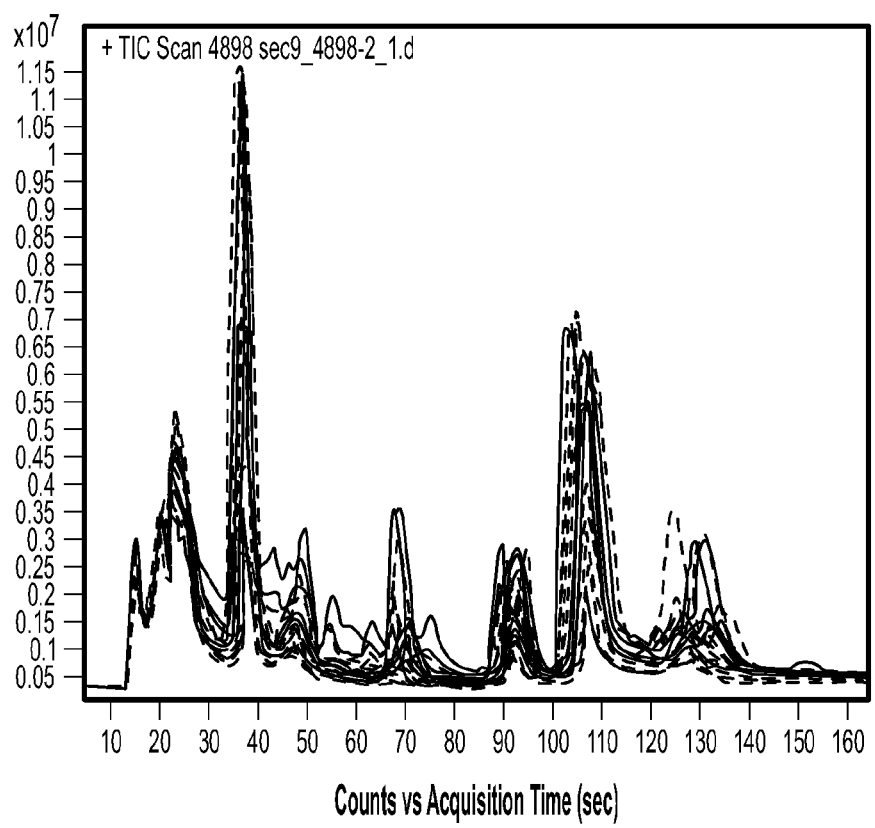

This invention is more particularly described below and the Examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The terms used in the specification generally have their ordinary meanings in the art, within the context of the invention, and in the specific context where each term is used. Some terms have been more specifically defined below to provide additional guidance to the practitioner regarding the description of the invention.

Autism remains a poorly-understood disease, particularly with regard to its etiology and the significance of any detectable alteration in brain chemistry to its etiology. A large number of changes in brain chemistry have been detected in autistic brains (all post-mortem), but without any consistent understanding of whether such changes are fundamentally related to development or progression of the disease or produced as a consequence thereof. The metabolomic signatures provided herein, on the other hand, reflect consistent differences in the autistic brains studied and identify particular metabolic pathways consistently associated with the disease.

The metabolome, defined as the total dynamic set of cellular metabolites present in cells or their surrounding matrix, is a product of health or disease/insult states. Metabolomics is particularly sensitive to environmental effects in comparison to other "omic" areas of study, such as genomics and proteomics. Cellular metabolites include but are not limited to sugars, organic acids, amino acids and fatty acids, particularly those species secreted, excreted or otherwise released from cells (e.g., as the result, inter alia, of chemical or physical trauma), that participate in functional mechanisms of cellular response to pathological or chemical insult. Such cellular metabolites, properly appreciated, can serve as biomarkers of disease or toxic response and can be detected in biological fluids (Soga et al., 2006, *J Biol Chem* 281:16768-78; Zhao et al., 2006, *Birth Defects Res A Clin Mol Teratol* 76:230-6). Within the "omics" sciences, it is postulated that metabolomics is the platform that is closest to the phenotype in comparison to other "omics," as it measures the end products of metabolism (Dettmer et al., 2007, *Mass Spectrom. Rev.* 26:51-78).

A metabolomic signature (i.e., a population of cellular metabolites) differentially produced by autistic patient biofluids provides a reliable diagnostic marker for detecting autism. Certain aspects of the invention provide assays of cellular metabolites using physical separation methods, including but not limited to liquid chromatography electrospray ionization time-of-flight mass spectrometry (ESI-TOF), for example. Metabolites can be identified using their exact molecular mass, as well as mass spectrometry fragmentation patterns of the metabolites. The sensitivity of applying such methods to detecting cellular metabolites produced by autistic patients provides improved identification of autistic disorders compared with less robust methods in the art, which have focused on psychological, developmental and behavioral assessments rather than metabolic biochemistry. Using a metabolomics diagnostic approach is a more reliable indicator of autistic phenotype versus gene specific diagnostics given the fact that not all changes in gene transcription correlate with a phenotype.

Additional embodiments of the invention include a metabolomic signature unique to autism. In one embodiment, a metabolic signature comprising one or more cellular metabolites, and in a particular embodiment, one or more cellular metabolites of the serotonin, cysteine, tryptophan, methionine, glutamate or GABA metabolic pathways, is provided herein. In certain embodiments, the metabolites comprising a metabolomic signature set forth herein comprise one or more of N-acetylaspartylglutamic acid, L-cystathionine, 2-aminooctanoic acid, 5-hydroxylysine, vinylacetylglycine, proline betaine, caffeine, 3-carboxy-1-hydroxypropylthiamine diphosphate, 3'-sialyllactosamine, 3,4-dihydroxybenzylamine, dipalmitoyl-phosphatidylcholine, SAICAR ((S)-2-[5-Amino-1-(5-phospho-D-ribosyl) imidazole-4-carboxamido]succinate), glutamate, or GABA intermediates. (e.g., metabolites involved in the anabolism or catabolism of GABA such as L-glutamine, L-glutamate, alpha-ketogluratate, succinic acid semialdehyde, 4-aminobutyraldehyde, 4-guanidinobutanoate, or L-ornithine Methods and reagents for identifying and measuring cellular and particularly biochemical effects of autism, are provided, including methods for diagnosing autism. The term "metabolite," "cellular metabolite" or the plural form, "cellular metabolites," as used herein refers to any molecule or mass feature in the range of about 10 Daltons to about 1500 Daltons secreted by a cell and present in a tissue sample or biofluid. A cellular metabolite can include but is not limited to the following types of molecules: acids, bases, lipids, sugars, glycosides, amines, organic acids, lipids, amino acids, oximes, esters, dipeptides, tripeptides, fatty acids, cholesterols, oxysterols, glycerols, steroids, and/or hormones. In one embodiment, the cellular metabolites can include but are not limited to N-acetylaspartylglutamic acid, L-cystathionine, 2-aminooctanoic acid, 5-hydroxylysine, vinylacetylglycine, proline betaine, caffeine, 3-carboxy-1-hydroxypropylthiamine diphosphate, 3'-sialyllactosamine, 3,4-dihydroxybenzylamine, dipalmitoyl-phosphatidylcholine, SAICAR ((S)-2-[5-Amino-1-(5-phospho-D-ribosyl) imidazole-4-carboxamido]succinate), glutamate, or GABA intermediates The phrases "identifying one or a plurality of cellular metabolites . . . differentially produced" and "differentially produces" as used herein include but are not limited to comparisons of cells or tissues from autistic humans with cells or tissues from non-autistic humans. Detection or measurement of variations in metabolite populations or mass features between autistic and non-autistic control samples are included in this definition. In a preferred embodiment, alterations in production of various metabolites are measured by determining a profile of changes in metabolite molecules in autistic versus control samples.

The term "physical separation method" as used herein refers to any method known to those with skill in the art sufficient to detect a profile of changes and differences in metabolites produced in the tissue or biofluid (e.g., lateral cerebellum, and post vermis brain, cerebrospinal fluid, blood, or plasma) of autistic humans according to the methods of this invention. In a preferred embodiment, physical separation methods permit detection of cellular metabolites including but not limited to sugars, organic acids, amino acids, fatty acids, hormones, vitamins, and peptides, as well as ionic fragments thereof and other cellular metabolites (preferably having a molecular weight less than 3000 Daltons, more particularly between 10 and 1500 Daltons, and even more particularly between 100 and 1000 Daltons). In certain embodiments, the physical separation method is liquid chromatography/electrospray ionization time of flight mass spectrometry (LC/ESI-TOF-MS) and/or hydrophilic interaction chromatography (HILIC), however it will be understood that cellular metabolites as set forth herein can be detected using alternative spectrometry methods or other methods known in the art for analyzing these types of cellular compounds in this size range.

Data for statistical analysis can be extracted from chromatograms (i.e., spectra of mass signals) using statistical analysis packages such as AGILENT® MASSHUNTER® software (Product No. G3297AA, Agilent Technologies, Inc. Santa Clara, Calif.); it will be understood that alternative statistical analysis methods can be used instead. Masses are advantageously binned together if they are within 10 ppm and eluted within a 2 minutes retention time window. A binned mass can be considered to be the same molecule across different LC/ESI-TOF-MS analyses (referred to herein as an "exact mass") if the detected masses are within ±10 ppm. Binning of the data is required for statistical analysis and comparison of masses across experiments. If multiple peaks with the same mass at the same retention time within a single sample were detected, for example, by MASSHUNTER® software, they can be averaged to assist data analysis. Masses lacking a natural isotopic distribution or with a signal-to-noise ratio of less than 3 are removed from the data prior to analysis. The results from these assays provided relative values that were assessed according to annotated values within 20 ppm and provided a putative identity for the molecular weight detected according to chemical databases. Thus, a mass shift within 20 ppm was considered consistent with determining the identity of a specific annotated cellular metabolite known in the art due to differences in ionization source and instrumentation, (e.g., between different experiments or using different instruments).

As used herein, a mass can be considered to be the same across separate LC/ESI-TOF-MS injections using an algorithm that first sorts the data by mass and retention time.

After sorting, a compound can be considered unique if it had a retention time difference of less than or equal to three minutes and a mass difference less than or equal to a weighted formula (0.00002× mass). If a series of measurements from different separations fit this definition said measurements are considered to arise from separation of the same compound. If either the mass or the retention time is found to vary by more than the limits listed above, the mass is considered to be a different compound and given its own unique designation.

Significance tests such as ANOVAs on the log base 2 can be used to transform abundance values of unique compounds present in autistic versus not-autistic sample a at each time point. A randomized complete block design using the ANOVA model including diagnosis, experiments, and a residual term, can be expressed using the following formula:

$$\text{Log}_2(\text{abundance}_{tb}) = \text{diagnosis}_t + \text{section}_b + \text{error}_{tb}.$$

Missing data are omitted from the test, changing the degrees of freedom (rather than assuming the missing data were absent). This assumption was made because the extensive filtering performed by the Mass Hunter software can miss or filter certain peaks because they are below a certain abundance threshold and not zero. The ANOVA F-test was considered significant if its p-value was less than 0.05. Fold changes were calculated using the least squared means for a given time and treatment.

The terms "metabolic signature" and "biomarker profile" as used herein refer to one or a plurality of metabolites identified by the inventive methods. Metabolic signatures and biomarker profiles according to the invention can provide a molecular "fingerprint" of autism spectral disorders and identify one or preferably a population of cellular metabolites significantly altered in individuals with autism spectral disorders. In preferred embodiments, metabolic signatures or biomarker profiles can be used to diagnose autism in an individual.

The term "biomarker" as used herein refers to cellular metabolites that exhibit significant alterations between diseased and controls. In preferred embodiments, biomarkers are identified as set forth above, by methods including LC/ESI-TOF-MS. Metabolomic biomarkers were identified by their unique molecular mass and consistency, thus the actual identity of the underlying compound that corresponds to the biomarker is not required for the practice of this invention. Alternatively, certain biomarkers can be identified by, for example, gene expression analysis, including real-time PCR, RT-PCR, Northern analysis, and in situ hybridization, but these will not generally fall within the definition of the term "cellular metabolites" as set forth herein.

Metabolite profiling as set forth herein was conducted on postmortem tissue as opposed to samples collected from live patients. Ultimately, biomarkers discovered in vivo are expected to be useful for analyzing samples such as biofluids including for example, cerebrospinal fluid, blood, plasma, amniotic fluid and urine, i.e., complex mixtures of extracellular biomolecules. This inventive methods are advantageous over invasive procedures such as tissue biopsies because metabolites in biofluids can be detected non-invasively (in contrast to intracellular compounds). In addition, processing cellular supernatant for mass spectrometry is more robust and less laborious than cellular extracts. However, cellular extracts from, for example, tissue biopsies or lysed cells, are encompassed in the methods of the invention. The terms "samples" or "biosamples" or "patient samples" include but are not limited to cerebrospinal fluid, brain tissue, amniotic fluid, blood, or plasma.

The identification of differential metabolites in the organ that is primarily affected in autism (brain) prior to biofluid analysis provides a targeted approach towards the development of novel diagnostics. Identifying specific biomarkers for autism in biofluids, such as cerebrospinal fluid, urine or plasma, without a defined set of candidates, would be particularly arduous. Biofluids are complex mixtures of systemic byproducts influenced by both endogenous and exogenous factors (genetics, diet, the environment). Using the methods of the current invention, specific analytical chemistry protocols can be used for assessing biofluids for defined exact mass and retention times of specific candidate biomarkers.

As set forth in more detail in the Examples below, analysis of fifteen fresh frozen samples from the Autism Tissue Program (ATP) (six autism and nine controls) using the methods described herein detected statistically-significant differences in the abundance of multiple metabolites between postmortem autistic and non-autistic brain samples. Preliminary experiments using hydrophilic interaction chromatography (HILIC) followed by positive mode ESI-TOF ionization identified a total of 98 metabolites that were differentially produced between autistic and non-autistic brains. For example, 5-hydroxylysine (exact mass 162.0981) displayed significant changes ($p<0.05$). Parallel preliminary experiments using C18 chromatography followed by positive mode ESI-TOF ionization, generated 47 statistically significant metabolites ($p<0.05$). The chemical identity of these metabolites can be definitively confirmed by tandem mass spectrometry (MS-MS).

Metabolites from fresh frozen postmortem brain were initially separated by liquid chromatography (LC) and then ionized and detected by electrospray ionization time of flight mass spectrometry (ESI-TOF-MS). This mass spectrometry modality was chosen because it is particularly suited for metabolomics of fresh frozen brain tissue: it is highly sensitive, detecting small molecule metabolites at very low abundances (e.g., micromolar to picomolar concentrations) and providing highly accurate measurements of the exact mass of metabolites with a resolution of 3 ppm. Other analytical chemistry platforms employed in metabolomics, such as NMR (nuclear magnetic resonance) are less sensitive than mass spectrometry, requiring larger amounts of biological samples to detect metabolites at significantly higher concentrations (reviewed in Glish et al., 2003, *Nat. Rev. Drug Discov.* 2:140-150). As set forth herein, metabolomics analysis of postmortem brain samples revealed a plurality of biochemical differences between autistic and non-autistic brains. The identification of cellular metabolites differentially secreted by autistic brain provide biomarkers for diagnosing autism, as set forth with particularity herein.

In certain embodiments, the invention provides the following metabolites, taken alone, as a population, or in any informative combination, as biomarkers of autism: N-acetylaspartylglutamic acid, L-cystathionine, 2-aminooctanoic acid, 5-hydroxylysine, vinylacetylglycine, proline betaine, caffeine, 3-carboxy-1-hydroxypropylthiamine diphosphate, 3'-sialyllactosamine, 3,4-dihydroxybenzylamine, dipalmitoyl-phosphatidylcholine, SAICAR ((S)-2-[5-Amino-1-(5-phospho-D-ribosyl)imidazole-4-carboxamido]succinate), glutamate, or GABA intermediates.

Abnormalities in neurochemical pathways have been hypothesized as a potential basis for the pathogenesis and/or clinical manifestation of autism. It has been speculated with varying amounts of supporting, generally anecdotal evidence that perturbations to serotonin, kynurenine, glutamate, cysteine, and methionine metabolism may play a role in autism. The methods provided herein and the biomarkers provided according to the practice of these methods in contrast, provides an experimental evidentiary basis for associating detection of one or a plurality of said biomarkers with the existence of autism or an autism spectrum disorder in an individual.

EXAMPLES

The Examples that follow are illustrative of specific embodiments of the invention, and various uses thereof. They are set forth for explanatory purposes only, and are not to be taken as limiting the invention.

Example 1

Preparation of Postmortem Brain Tissue

Postmortem brain tissue from autistic patients and age-matched controls was obtained from the Autism Tissue Program (ATP). Altogether, 6 autistic and 9 non-autistic postmortem brain samples from the University of Maryland Brain and Tissue Bank for Developmental Disorders were studied (See Table 1). Metabolomics was performed with fresh frozen sections of the lateral cerebellum and post vermis from the above-mentioned samples. The cerebellum was selected because it is a region where abnormal neuroanatomical findings most consistent in autistic patients are localized (Kemper et al., 1998, *J. Neuropathol. Exp. Neurol.* 57:645-652). Differences in age, PMI (postmortem interval) and degree of clinical manifestation were acknowledged to be a source of variability in the abundance and nature of metabolites measured by metabolomics.

Prior to metabolomics, frozen brain specimens were mounted on the pre-cooled stage of a Leica SM200R microtome using 30% sucrose and sectioned to create uniform samples weighing ~50 mg. Metabolites were extracted in 80% methanol/20% 0.5% formic acid on a volume per wet tissue weight ratio by homogenizing the sample in a conical glass homogenizer. The samples were then stored at −20° C. for 30 minutes to precipitate proteins and insoluble material. Thereafter, the cold incubation samples were centrifuged at 16,000×g for 25 minutes at 4° C. to pellet cell debris, proteins, and other insoluble material. Supernatant was then transferred to a new tube, and re-extracted with 300 µl of extraction buffer. Samples were dried in a rotary evaporator for 6-7 hours until dry to remove the extraction buffer. Extracts were then dissolved in 500 µl of 20% acetonitrile/80% 0.1% formic acid and centrifuged through a Millipore 3 kDa MICROCON® column (Millipore) for three hours at 13,000×g to remove large molecular weight (>3 kDa) biomolecules. Flowthrough was dried in a rotary evaporator and dissolved in 2 µ/mg 95% 0.1% formic acid/5% acetonitrile and stored at −80° C. prior to analysis by LC-MS.

Liquid chromatography electrospray-ionization time-of-flight mass spectrometry (LC-ESI-TOF-MS) was performed on these extracts using an AGILENT® QTOF LC/MS system consisting of a G6520AA QTOF high resolution mass spectrometer capable of exact mass MS and MS/MS ion fragmentation. The polar metabolite fraction of each sample was analyzed using two different chromatographic methods for maximal separation and small molecule resolution: a) 3×100 mm PHENOMENEX® 3 µm Luna hydrophilic interaction chromatography (HILIC) and b) 2.1×50 mm ZORBAX® 1.8 µm C18-SB columns (C18). This approach maximized the number of metabolites that were separated and subsequently ionized and measured. Ultra high pressure liquid chromatography (UPLC) analysis was performed with the ZORBAX® C18 column using a 15 minute gradient from 5% acetonitrile/95% water/0.1% formic acid to 100% acetonitrile/0.1% formic acid at a flow rate of 400 µl/min. The HILIC HPLC method was performed using a 16 minute gradient from 95% acetonitrile/5% water/0.1% formic acid to 60% acetonitrile/40% water/0.1% formic acid with a 500 µl/min flow rate. Electrospray ionization was employed using a dual ESI source, with an AGILENT® isocratic pump continuously delivering an internal mass reference solution into the source at approx. 0.01 ml/min. The mass range of the instrument was set at 75-1500 Da and data were acquired in 2 GHz mode to maximize dynamic range. Data acquisition was performed with AGILENT® MASSHUNTER® version B.02.00 using high-resolution exact mass conditions.

Example 2

Identification of Metabolites Differentially Produced in Autistic Brain

Prior to data analysis, total ion chromatogram (TIC) of each sample was carefully inspected for quality and reproducibility of the MS signal. For those samples wherein the TIC abundance deviated by more than 25% from the median across the LC-MS gradient, LC-MS analysis was repeated (FIG. 1). Data was deisotoped and then converted into the open source mzData format.

Data analysis was performed using the open source statistical programming and analysis software R. The XCMS package (Smith et al., 2006, Anal. Chem. 78:779-787) was used to analyze the LC-ESI-TOF-MS resulting files using the Centwave algorithm for peak peaking (Tautenhahn et al., 2008, BMC Bioinf. 9:504). Retention time deviations across LC-MS samples were corrected using rector (retention time correction) loess regression of features common to all LC-MS samples and the features grouped using the density based functions in XCMS. The maximum observed deviation for HILIC chromatography was 15 seconds and 4 seconds for C18 chromatography. After the grouping function was performed features missing in LC-MS samples were iteratively integrated using m/z and retention time windows based on the range of the feature group. The peak intensity tables were evaluated using both univariate and multivariate statistical analysis. Contaminant ions were removed by comparing brain tissue extracts to mock extraction blanks Features present in both the brain tissue extracts and the mock extraction blanks were removed from the data set if their abundance was less than five-fold greater than the extraction blank. Statistical significance of individual mass features was performed under the null hypothesis that no difference in their abundance existed between control and autistic post mortem brains. Differential metabolites, or features, were determined using an incomplete block design ANOVA with the model log 2(abundance)~section+diagnosis on the combined brain regions. Features were considered statistically significant if they exhibited a fold change greater than 25% and a p value less than 0.05 in the diagnosis factor of the ANOVA model. The extracted ion chromatogram of each statistically significant feature was further evaluated to confirm an observable difference between autistic and normal extracts to reduce the inclusion of spurious results.

Direct injections were analyzed using the Continuous Wavelet Transform (Du et al., 2006, *Bioinformatics*, 22:2059-2065) peak picking algorithm in XCMS. AGI- LENT® Mass Qualitative Analysis Software Version 2.00B was used to convert vendor specific raw data files into open source mzData files. Features with a height of equal to or greater than 1000 were included for analysis and then deisotoped prior to identifying mass features. The generation of mass features (putative metabolites) was implemented using methods present in the XCMS (Smith et al., 2006, *Anal., Chem.* 78:779-787) library from R/Bioconductor. Each ESI polarity was processed independently. The centwave algorithm (Tautenhahn et al., 2008, BMC Bioinf. 9:504) designed for the detection of peaks in high resolution high mass accuracy data was utilized for peak picking. The input variables for the centwave algorithm were based on QTOF settings and the chromatography method. Following peak picking deviations in retention times were corrected using loess regression. Mass feature bins or groups were generated using the density based grouping algorithm using parameters optimized for LC-MS gradients. After data had been grouped into mass features, missing features were integrated based on retention time and mass range of a feature using the iterative peak filling method in XCMS.

Binning of mass features detected in individual LC-MS was used to identify features that were present at the same retention time across injections. A binning algorithm based on both exact mass and retention time was used to consider a mass feature to be the same across different LC/ESI-MS-QTOF experiments. Binning criteria were based on both a sliding mass difference scale that allowed for larger mass differences at lower molecular weights and a constant retention time window based on the reproducibility of the chromatography.

Statistical significance testing of individual mass features was performed under the null hypothesis that no difference in their abundance existed between control and autistic vermis samples using a permutation based test statistic. This analysis was performed by exploring different combinations of metadata in the loading and scores plots using the pcaMethods library in R (Stacklies et al., 2007. PcaMethods: A collection of PCA methods. R package version 1.12.0. Available from CRAN.R-project.org/). General differences between control and autism postmortem brain samples were evaluated using Welch t-tests. Bayesian principal component analysis was performed because this method can tolerate missing data (Oba et al., 2003, *Bioinformatics*, 19:2088-2096) when determining whether global changes in metabolism existed between control and autistic brain tissue. This analysis was performed by exploring different combinations of metadata in the loading and scores plots using the pcaMethods library in R (Stacklies et al., 2007. Pca Methods: A collection of PCA methods. R package version 1.12.0. Available from CRAN.R-project.org/).

Statistically significant features were also modeled using Principal Cluster Analysis (PCA)-based methods and hierarchical clustering to examine their ability to classify the samples in an unsupervised manner. As a result, a comprehensive list of low metabolites that were statistically significantly different between postmortem autistic brains and non-autistic controls were identified following statistical analysis of an average of 6,000 features per experiment. Mass spectrometry based metabolomic profiling, or metabolomics, revealed significant changes (p-value<0.05) in autistic brains in 98 metabolites using HILIC and 47 metabolites using C18 chromatography.

TABLE 1

Autism Tissue Program (ATP) approved postmortem samples subject to LC-ESI-TOF-MS metabolomics for identifying metabolites and pathways that are statistically significantly altered in autistic brain.

| UMB# | Frozen Vermis | Lateral Hem | Diagnosis | Sex | Age Yrs | Days | Age | PMI (Hours) |
|---|---|---|---|---|---|---|---|---|
| 1182 | + | + | Autism | F | 9 | 354 | 9.97 | 24 |
| 1185 | + | + | Control | M | 4 | 258 | 4.71 | 17 |
| 1349 | + | + | Autism | M | 5 | 220 | 5.60 | 39 |
| 1407 | + | − | Control | F | 9 | 46 | 9.13 | 20 |
| 1500 | + | + | Control | M | 6 | 320 | 6.88 | 18 |
| 1541 | + | + | Control | F | 20 | 228 | 20.62 | 19 |
| 1638 | + | + | Autism | F | 20 | 277 | 20.76 | 50 |
| 1674 | + | + | Control | M | 8 | 339 | 8.93 | 36 |
| 1706 | + | + | Control | F | 8 | 214 | 8.59 | 20 |
| 1708 | + | + | Control | F | 8 | 50 | 8.14 | 20 |
| 1860 | − | + | Control | M | 8 | 2 | 8.01 | 5 |
| 4231 | + | + | Autism | M | 8 | 300 | 8.82 | 12 |
| 4671 | + | + | Autism | F | 4 | 165 | 4.45 | 13 |
| 4721 | + | + | Autism | M | 8 | 304 | 8.83 | 16 |
| 4898 | + | + | Control | M | 7 | 272 | 7.75 | 12 |
| 15 | 14 | 14 | Autism = 6 | 8 Male | | | | |
| | | | Control = 9 | 7 Female | | | 9.19 | 18.56 |

UMB# represents archival sample number.

Example 3

Chemical Annotation of Autism-Specific Metabolites

Following identification of metabolites differentially secreted in autistic cerebelli as described in Example 2, chemical annotation of these molecules was further refined by ion fragmentation pattern analysis (MS-MS). Specifically, fragmentation patterns and retention times of each small molecule identified above were compared to analytical grade chemical standards. While confirmation of the chemical identity of each small molecule is not required for autistic biomarker determination, annotated identity is advantageous in that it provides more uniform nomenclature for each small molecule biomarker. Subsequent chemical identification of the differentially produced metabolites also permits in silico mapping of metabolites onto specific pathways via bioinformatics (GeneGo software). This information thus revealed systematic metabolic pathways and/or networks that underlie biochemical differences between postmortem brains of autistic and non-autistic age matched controls.

The neutral exact mass of each compound was queried against the public searchable databases METLIN (metlin.scripps.edu), The Human Metabolome Database (www.hmdb.ca), and the Kyoto Encyclopedia of Genes and Genomes (www.genome.jp/kegg/), or the Biological Magnetic Resonance Bank (www.bmrb.wisc.edu/metabolomics/) for candidate identities. Measured mass features are considered to match a metabolite present in the databases if their exact masses were within 20 parts per million of the annotated database molecule (0.00002× mass). The chemical identity of the biomarker candidates was confirmed using one or more of the following three criteria: (1) molecular exact mass, (2) MS/MS fragmentation pattern and (3) chromatographic retention time. The exact mass of each candidate biomarker (i.e., mass feature), as determined by interpretation of electrospray ionization time of flight mass spectrometry (LC-ESI-TOF MS/MS) (i.e., tandem mass spectrometry) data was queried against the various public searchable databases set forth above for putative molecular identities Annotated candidates were then validated by acquiring MS/MS product ion spectra for the candidate molecular ion, then matching the MS/MS fragmentation pattern for product ion spectra obtained for a known analytical grade standard reference compound (Cummings et al., 2009, *J Chromatogr B Analyt Technol Biomed Life Sci.*, 877:1221).

Analytical grade chemical standards for L-cystathionine, 2-aminooctanoic acid and N-acetylaspartylglutamic acid were purchased from Sigma Chemical Co., St. Louis, Mo. for comparative mass spectrometry. Chemical references were evaluated using identical chromatographic methods used in the metabolomic analysis of the original samples. Additionally, seven of the original samples (4 autistic and 3 control) were re-analyzed for comparison with the chemical standards, to ensure retention time and ion fragmentation match. Chemical references were dissolved in appropriate buffers and 100 µM standards were prepared by diluting into 95% 0.1% formic acid/5% acetonitrile. The experimental samples and chemical standards were fragmented using the following formula to determine collision energy: Collision Energy=(m/z of precursor-100)/100*3V+10V. A putative annotation was considered correct if the retention time and fragmentation pattern in the original sample matched the chemical references. If the putative metabolite was insufficiently abundant in the sample extract to be fragmented, the retention time alone was used to confirm annotation.

The third confirmation criterion was established by co-injecting (i.e., spiking) endogenous metabolites with a known reference compound to determine whether the chromatographic retention time and ionization fragmentation patterns (FIG. 2) of the chemical standard matched the retention time of the biomarker candidate. Tandem mass spectrometry, or MS-MS, was used to confirm the identity of an endogenous metabolite in these experiments. After data analysis was completed, a subset of statistically significant metabolites was selected for confirmation against known chemical standards.

Figure 2A:
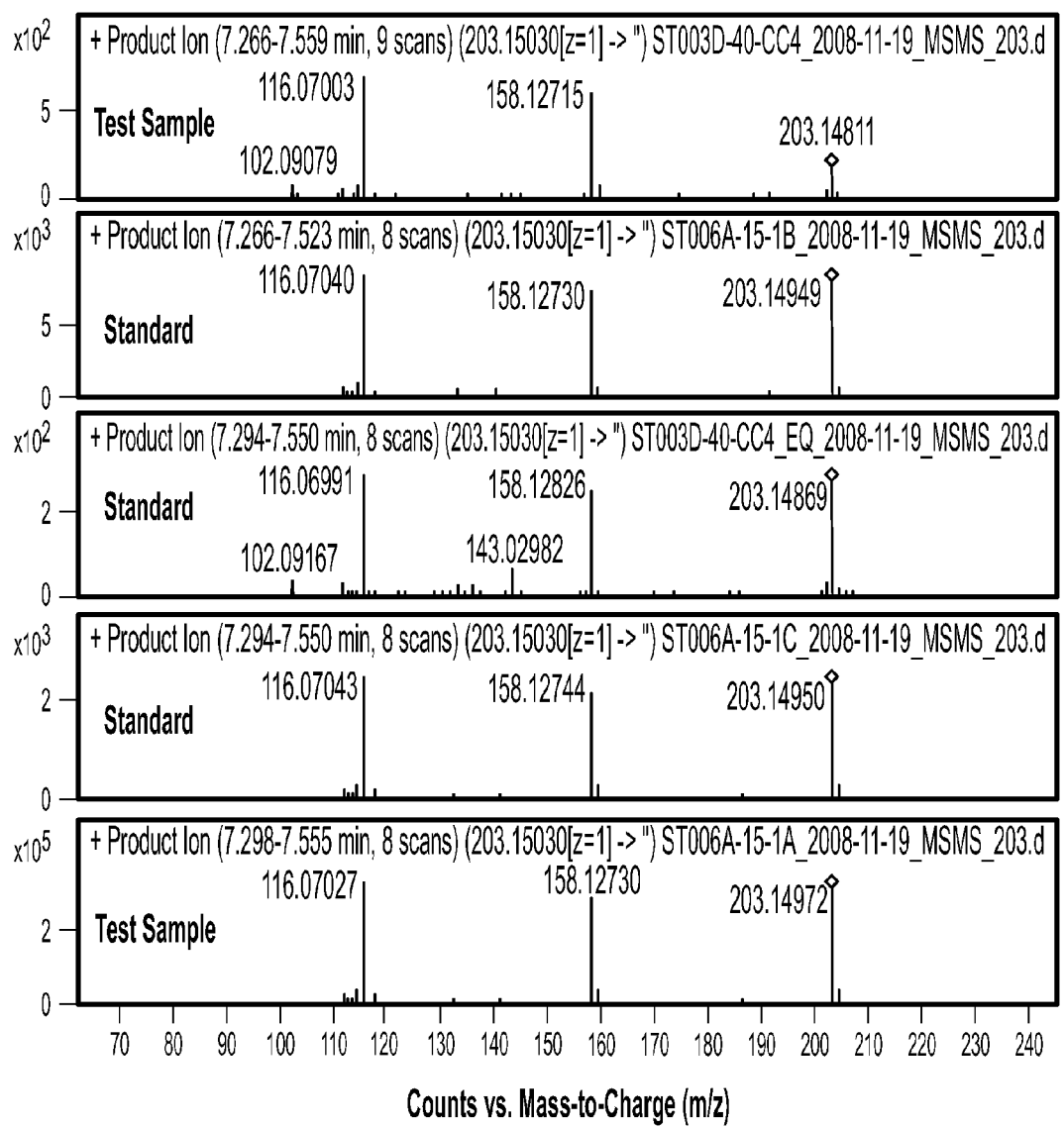
FIG. 2 (A) and FIG. 2 (B) are ion chromatogram controls that verified the chemical identities of test sample metabolites by comparative ion fragmentation pattern (FIG. 2 (A)) and retention time (FIG. 2 (B)) in the presence of standard chemical controls.
Figure 2B:
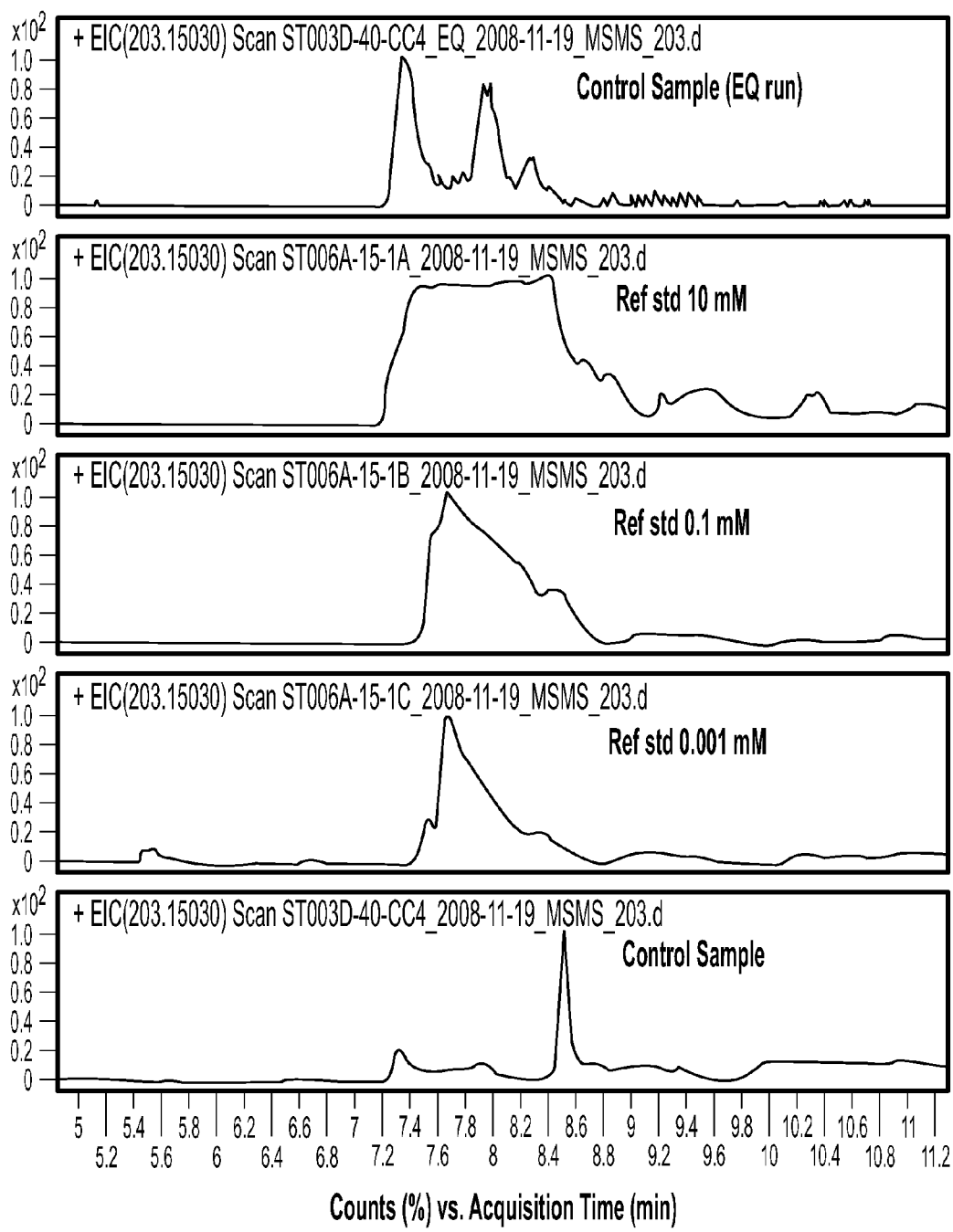

In these assays, fresh frozen brain extracts used to identify mass features as discussed above were spiked with 1 mM of the chemical standards and then analyzed by MS-MS. Remaining unused samples or spiked samples were processed by LC-ESI-MS/MS to confirm the structure and abundance of the ions of the putatively-identified compounds. Standards used as controls in these experiments had known retention times. Parallel retention times observed in spiked samples provided additional confirmation of metabolite identity. Final confirmation of chemical identity of candidate biomarkers was made upon both detection of fragment ions (FIG. 2, A) and retention time (FIG. 2, B). Classification of hits was based on a "shared peak count" method that identified masses of fragment ions shared between the analytical (fresh frozen brain extract) and chemical reference MS/MS spectra.

Statistically significant differences were detected in the abundance of multiple metabolites between postmortem autistic and non-autistic brain samples (Table 2). To focus on meatbolites that have a high probability of being significant, and to eliminate potential spurious artifacts, each data set (HILIC and C18 chromatography) was filtered using a moderate filter of a 25% fold change in abundance between control and autistic brain samples. HILIC chromatography followed by positive mode ESI-QTOF ionization identified 988 mass features exhibiting a fold change greater than 25%, of which 98 metabolites were statistically significantly different ($p<0.05$) between autistic and non-autistic brains. Additionally, C18 chromatography followed by positive mode ESI-QTOF ionization measured 938 mass features with at least a 25% fold change, generating 47 statistically significant metabolites ($p<0.05$). Table 2 shows a subset of the measured significant metabolites that have at least a 25% change in abundance between autistic and control postmortem brain samples with a corresponding extracted ion chromatogram (EIC) displaying a marked difference between autistic and control brain samples. One of the most challenging aspects of metabolomics studies is that many of the small molecules measured are yet not annotated in public databases. While current methods allow the identification of small molecule metabolites by unique mass, the identification by compound name is more challenging. The metabolites identified represent novel biomarkers, and importantly point to additional pathways contributing to the etiology of autism.

TABLE 2

Metabolites that exhibited significantly different levels between postmortem autistic and non-autistic brain samples.

| Exact Neutral Mass | Retention time (minutes) | Alteration in autistic brain samples | Putative Annotation | Biochemical Pathway | p-value |
| --- | --- | --- | --- | --- | --- |
| C18 Chromatography | | | | | |
| 136.5265 | 1.48 | ↑ | Unspecified | | 0.049 |
| 143.0939 | 0.33 | ↓ | Vinylacetylglycine/ Proline Betaine | Homocysteine | 0.01 |
| 159.1253 | 2.72 | ↓ | DL-2-Aminooctanoic acid (Confirmed) | | 0.02 |
| 173.0308 | 0.33 | ↓ | Unspecified | | 0.04 |
| 180.0640 | 0.93 | ↓ | Unspecified | | 0.0005 |
| 194.0805 | 3.62 | ↓ | Caffeine | | 0.034 |
| 279.1636 | 0.4 | ↓ | Unspecified | | 0.03 |
| 286.1751 | 2.06 | ↑ | Unspecified | | 0.012 |
| 321.0561 | 1.5 | ↑ | Unspecified | | 0.02 |
| 356.2055 | 3.16 | ↑ | Unspecified | | 0.05 |
| 363.1455 | 1.33 | ↑ | Unspecified | | 0.05 |
| 366.1421 | 0.58 | ↑ | Unspecified | | 0.016 |

TABLE 2-continued

Metabolites that exhibited significantly different levels between postmortem autistic and non-autistic brain samples.

| Exact Neutral Mass | Retention time (minutes) | Alteration in autistic brain samples | Putative Annotation | Biochemical Pathway | p-value |
|---|---|---|---|---|---|
| 382.8678 | 1.22 | ↑ | Unspecified | | 0.035 |
| 408.2181 | 5.58 | ↓ | Unspecified | | 0.029 |
| 422.2482 | 4.83 | ↑ | Unspecified | | 0.023 |
| 426.1936 | 4.67 | ↑ | Unspecified | | 0.039 |
| 531.2841 | 1.14 | ↑ | Unspecified | | 0.049 |
| 597.2905 | 6.98 | ↓ | Unspecified | | 0.012 |
| 599.3340 | 1.07 | ↑ | Unspecified | | 0.032 |
| 632.2266 | 0.56 | ↑ | 3-carboxy-1-hydroxypropylthiamine diphosphate/3'-Sialyllactosamine | | 0.037 |
| 806.0834 | 5.18 | ↓ | Unspecified | | 0.027 |
| 823.0550 | 6.85 | ↑ | Unspecified | | 0.016 |
| 823.7238 | 6.85 | ↑ | Unspecified | | 0.034 |
| HILIC Chromatography | | | | | |
| 87.0139 | 8.74 | ↑ | 3,4-Dihydroxybenzylamine | | 0.02 |
| 133.0168 | 8.74 | ↑ | Unspecified | | 0.008 |
| 133.0195 | 8.98 | ↑ | Unspecified | | 0.016 |
| 139.0609 | 1.33 | ↓ | Unspecified | | 0.03 |
| 143.0922 | 2.55 | ↓ | Unspecified | | 0.049 |
| 162.0981 | 9.37 | ↑ | 5-hydroxylysine | | 0.008 |
| 222.0628 | 8.74 | ↑ | L-Cystathionine (Confirmed) | Tryptophan | 0.019 |
| 241.1764 | 5.76 | ↓ | Unspecified | | 0.019 |
| 255.0853 | 5.16 | ↑ | Unspecified | | 0.039 |
| 304.0909 | 1.23 | ↑ | N-Acetylaspartylglutamic acid (Confirmed) | Neuropeptide | 0.054 |
| 309.9921 | 5.68 | ↓ | Unspecified | | 0.046 |
| 317.1924 | 5.87 | ↑ | Unspecified | | 0.002 |
| 364.0987 | 4.07 | ↑ | Unspecified | | 0.042 |
| 418.0277 | 3.37 | ↑ | Unspecified | | 0.018 |
| 430.1120 | 7.66 | ↑ | Unspecified | | 0.047 |
| 438.0307 | 2.58 | ↑ | Unspecified | | 0.013 |
| 454.0045 | 2.6 | ↑ | Unspecified | | 0.02 |
| 454.0692 | 4.04 | ↑ | SAICAR | | 0.042 |
| 464.0335 | 3.36 | ↑ | Unspecified | | 0.018 |
| 473.2109 | 4.06 | ↑ | Unspecified | | 0.025 |
| 501.9891 | 3.34 | ↑ | Unspecified | | 0.012 |
| 517.1560 | 4.09 | ↑ | Unspecified | | 0.027 |
| 522.0543 | 4.02 | ↑ | Unspecified | | 0.012 |
| 527.0686 | 2.63 | ↑ | 3-carboxy-1-hydroxypropylthiamine diphosphate | | 0.014 |
| 538.0278 | 3.96 | ↑ | Unspecified | | 0.007 |
| 543.0427 | 2.89 | ↑ | Unspecified | | 0.017 |
| 547.9951 | 3.41 | ↑ | Unspecified | | 0.008 |
| 568.0602 | 4.03 | ↑ | Unspecified | | 0.004 |
| 585.1485 | 4.10 | ↑ | Unspecified | | 0.035 |
| 590.0422 | 4.02 | ↑ | Unspecified | | 0.001 |
| 616.9752 | 2.61 | ↑ | Unspecified | | 0.015 |
| 636.0475 | 4.07 | ↑ | Unspecified | | 0.032 |
| 645.1668 | 7.67 | ↑ | Unspecified | | 0.041 |
| 658.0298 | 4.06 | ↑ | Unspecified | | 0.031 |
| 668.0565 | 2.79 | ↑ | Unspecified | | 0.044 |
| 674.0040 | 4.01 | ↑ | Unspecified | | 0.015 |
| 733.5650 | 0.79 | ↓ | Dipalmitoyl-phosphatidylcholine | | 0.044 |
| 811.0869 | 4.15 | ↑ | Unspecified | | 0.038 |
| 860.2212 | 7.68 | ↑ | Unspecified | | 0.042 |
| 882.1976 | 7.67 | ↑ | Unspecified | | 0.049 |

Chemical Annotation of Differentially Secreted Metabolites

Chemical annotations were confirmed for the following subset of differentially secreted metabolites.

L-cystathionine

Figure 3A:
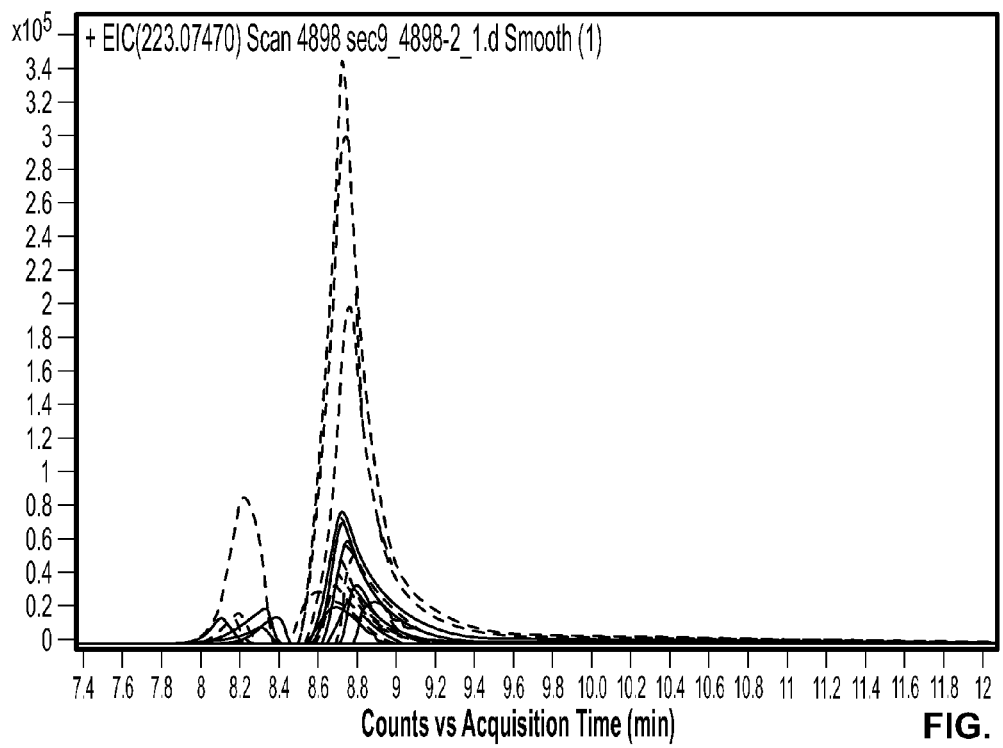
FIG. 3 (A)-FIG. 3 (C) are extracted ion chromatograms (EICs) of L-cystathionine, and FIG. 3 (D) is a plot of the relative abundance of L-cystathionine in autistic and control brain samples.
Figure 3B:
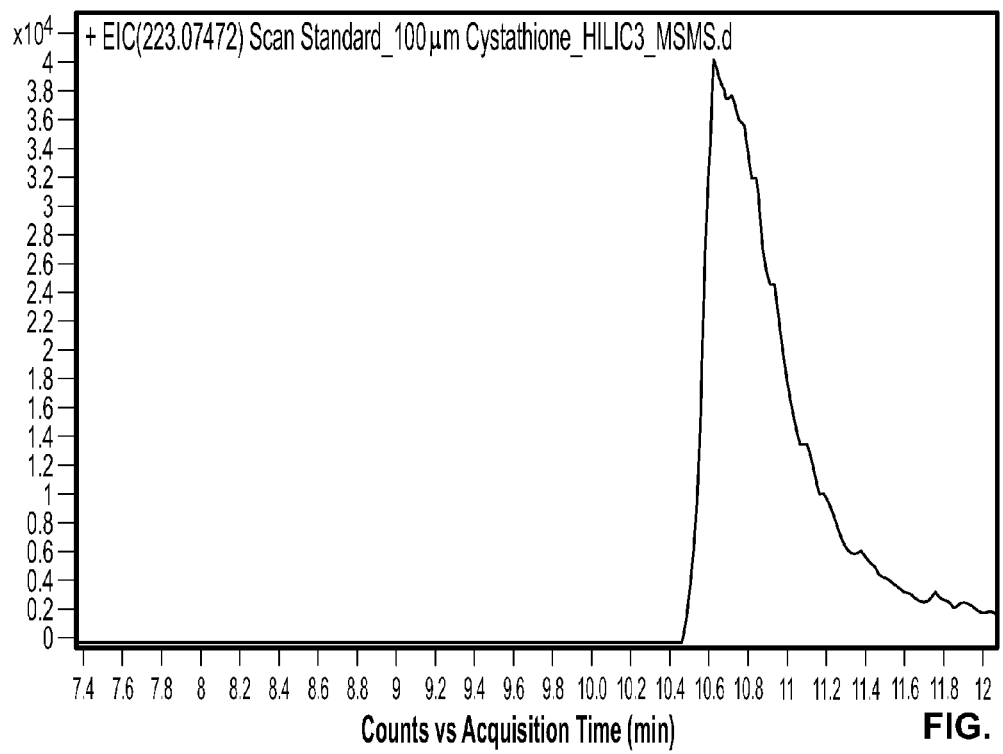
Figure 3C:
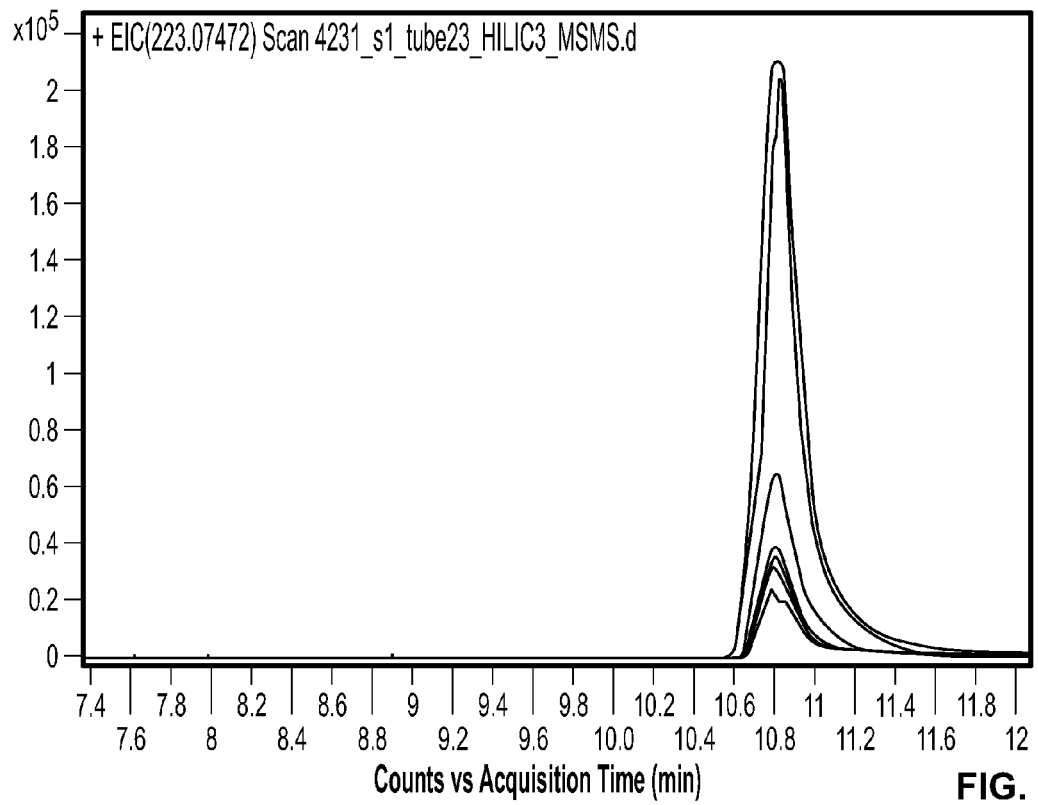
Figure 3D:
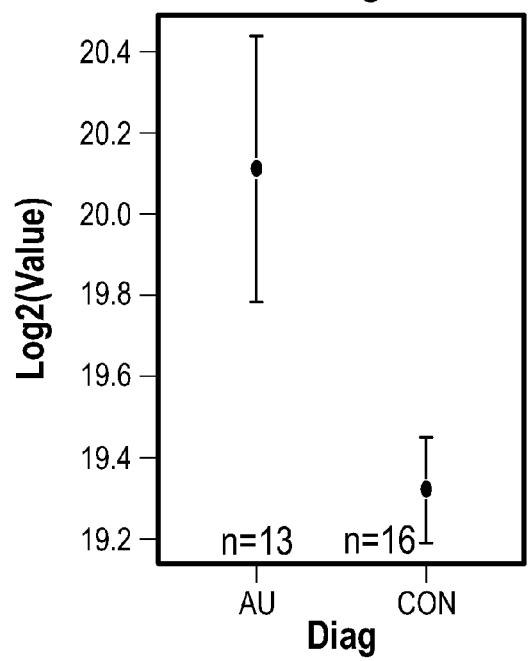
Figure 4A:
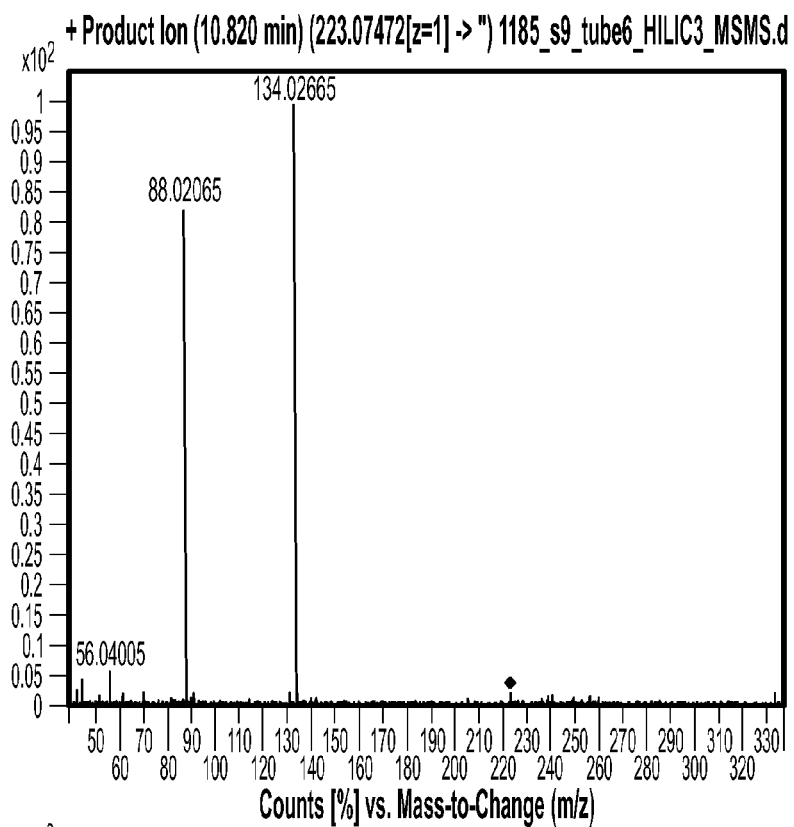
FIG. 4 (A)-FIG. 4 (D) are extracted ion chromatograms of L-cystathionine and N-acetylaspartylglutamic acid. Liquid chromatography electrospray ionization time-of-flight-mass spectrometry (LC-ESI-TOF-MS)/MS fragmentation of L-cystathionine in brain samples (FIG. 4 (A)) and chemical standards (FIG. 4 (B)) have matching fragmentation patterns, confirming the identity of L-cystathionine. The identity of N-acetylaspartylglutamic acid was confirmed by a matching MS/MS fragmentation pattern of brain (FIG. 4 (C)) and chemical standard (FIG. 4 (D)).
Figure 4B:
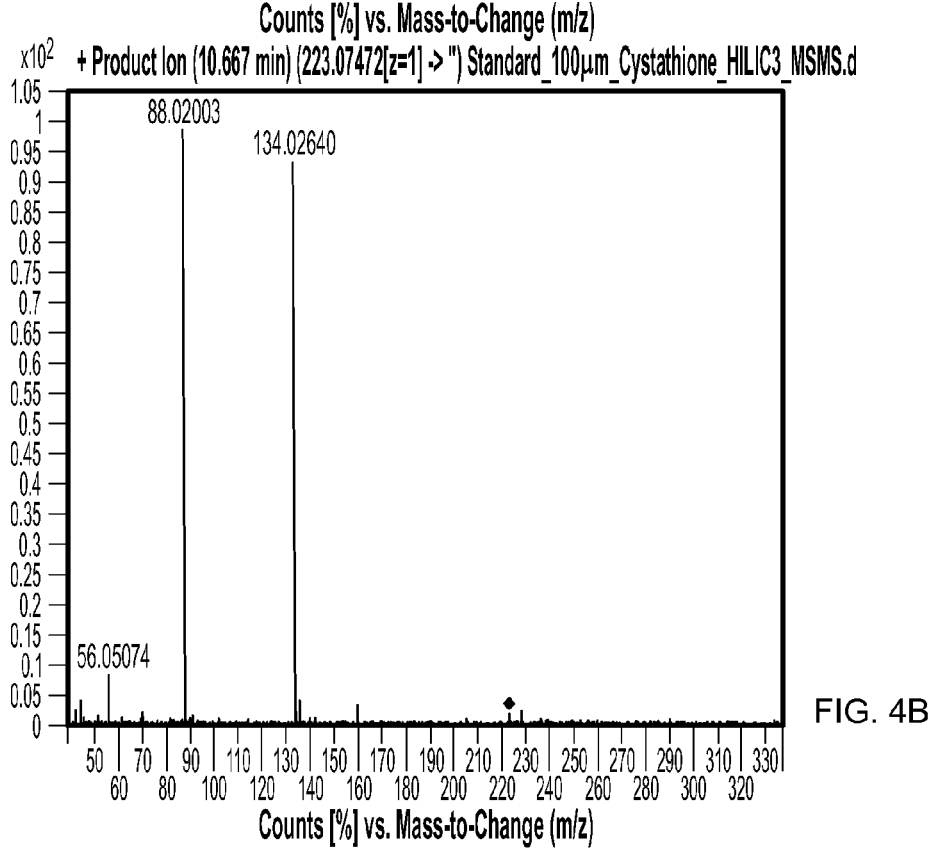

Several metabolites in the cysteine and methionine metabolic pathway were significantly elevated in autistic brains in comparison to controls. Using HILIC chromatography, a statistically significant difference was detected for L-cystathionine (exact mass 222.067) in both the post vermis and lateral cerebellum of autistic brain samples (p=0.019, FIGS. 3(A) and 3(D)). The chemical identity of L-cystathionine was secondarily confirmed by comparison of the retention time (FIGS. 3(B) and 3(C)) and ion fragmentation pattern between the postmortem brain samples (FIG. 4(A)) and the chemical standard (FIG. 4(B)).

2-Aminooctanoic Acid

Figure 5A:
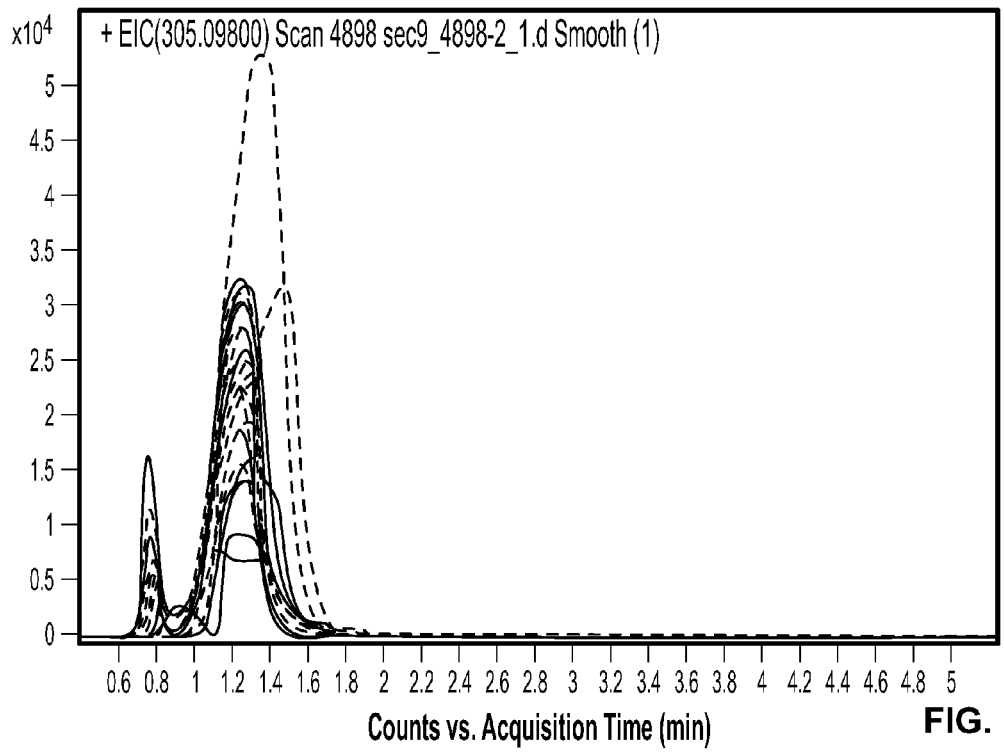
FIG. 5 (A)-FIG. 5 (C) are extracted ion chromatograms (EICs) of 2-aminooctanoic acid, and FIG. 5 (D) is a plot of the relative abundance of 2-aminooctanoic acid in autistic and control brain samples.
Figure 5B:
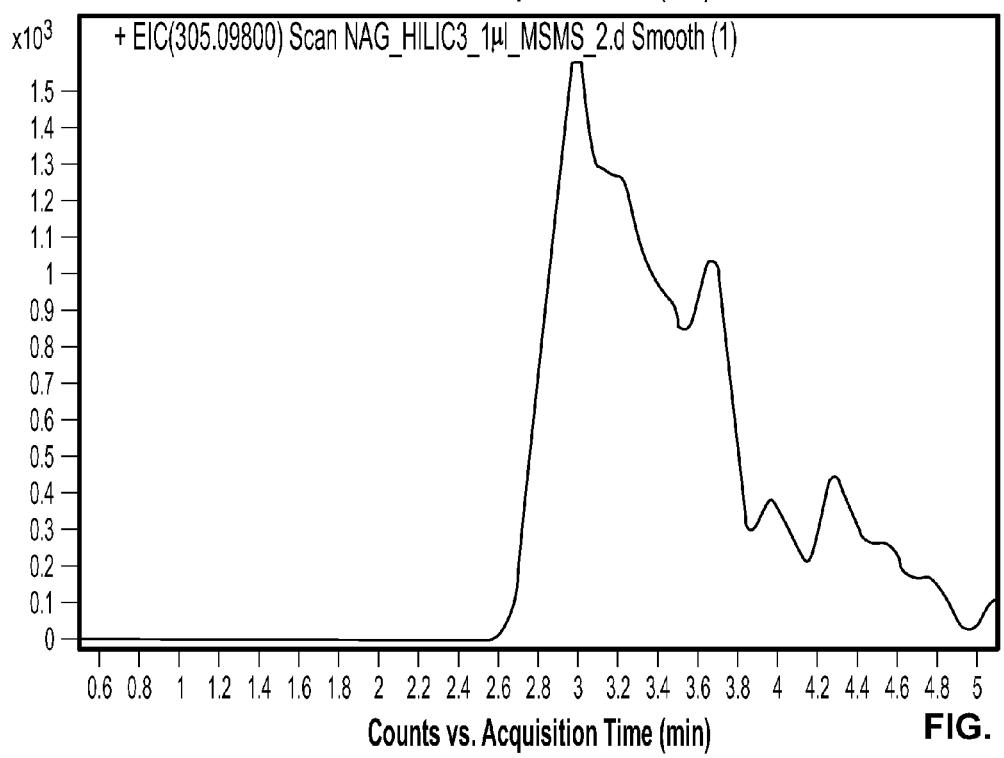
Figure 5C:
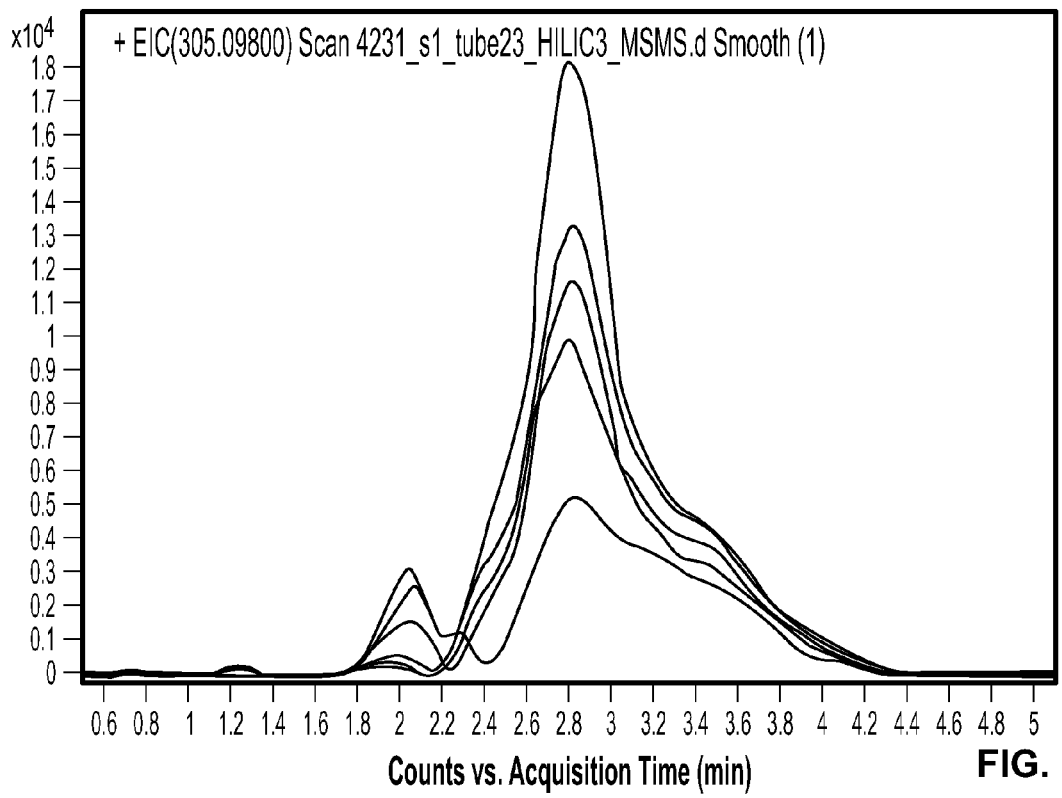
Figure 5D:
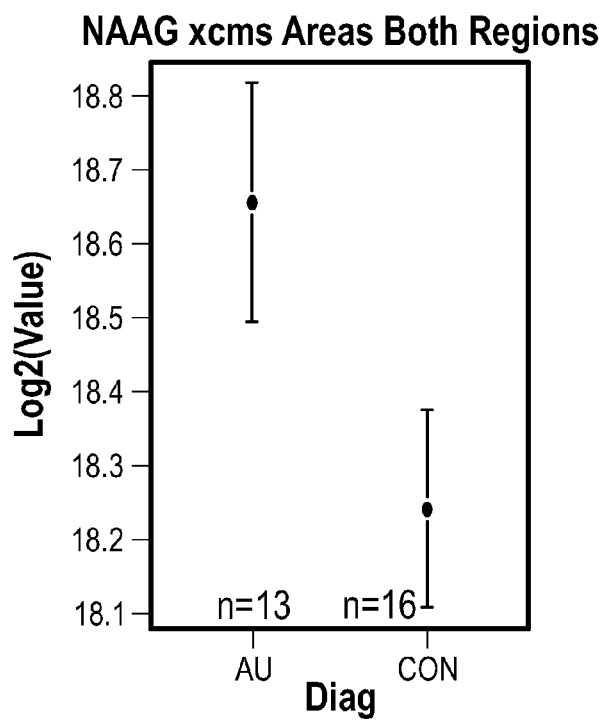

In contrast to L-cystathionine, the abundance of the metabolite 2-aminooctanoic acid (exact mass 159.125) was significantly reduced in both the post vermis and lateral cerebellum of autistic patients (p=0.027, FIGS. 5(A) and 5(D)). The global brain decrease in 2-aminooctanoic acid was 144% between autistic and control samples. 2-aminooctanoic acid has not been previously studied in brain samples, and thus the first evidence that alterations in 2-aminooctanoic acid concentration is related to autism is provided herein. Previous studies have only reported and measured this compound in urine (Parry et al., 1957, *Clinica Chimica Acta*, 2:115-125). Comparative mass spectrometry between the chemical standard (FIG. 5(B)) and postmortem brain samples (FIG. 5(C)) demonstrated a match in metabolite retention time. The low abundance range of 2-aminooctanioc acid in postmortem brain samples was an impediment to obtaining its ion fragmentation according to the standard MS-MS method employed for other metabolites in this study.

N-Acetylaspartylglutamic Acid (NAAG)

Figure 4C:
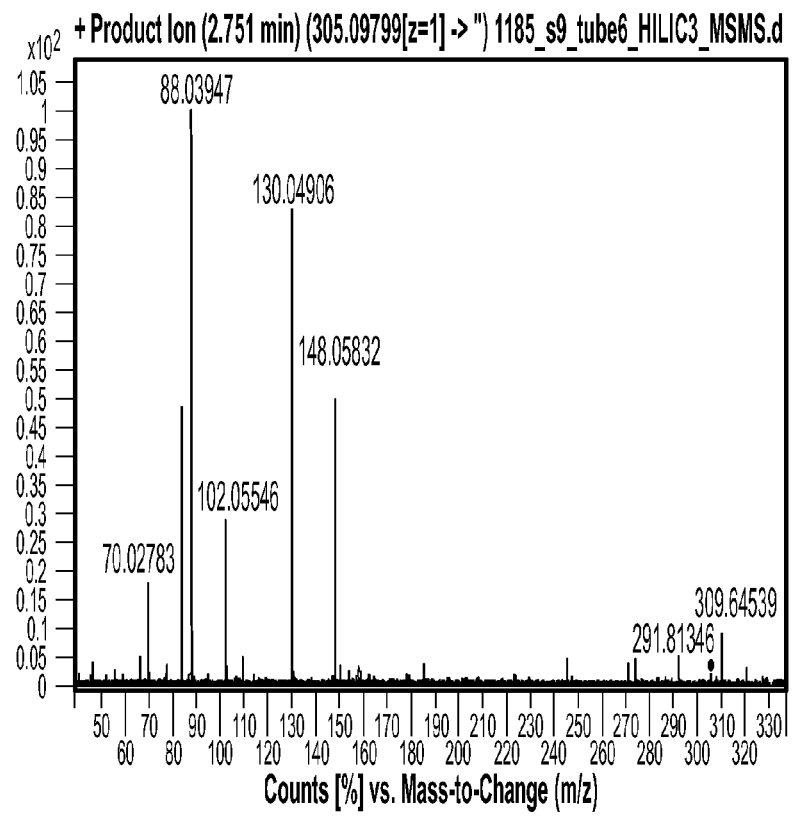
Figure 4D:
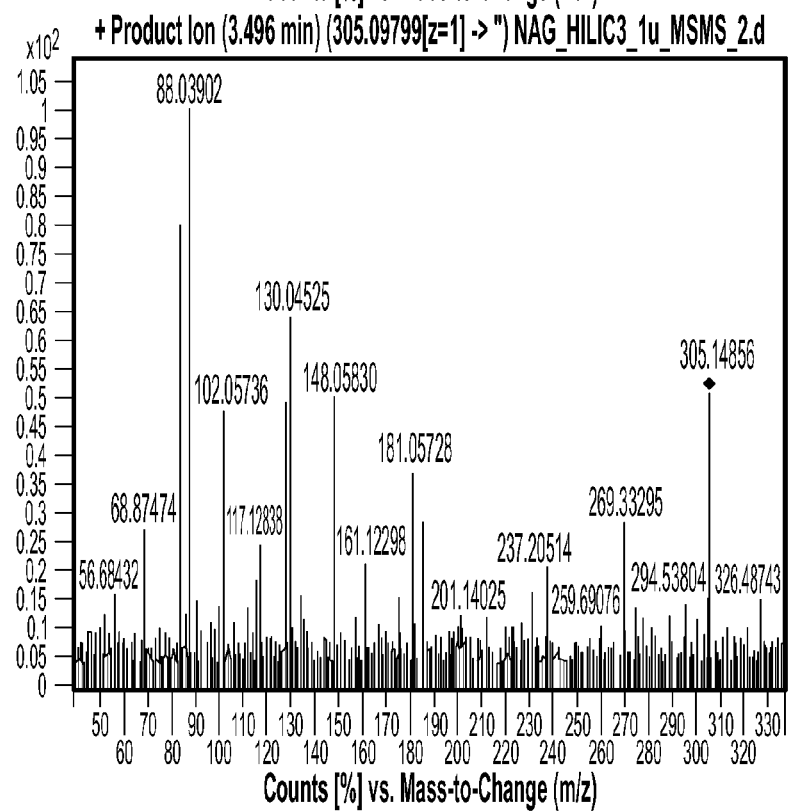
Figure 6A:
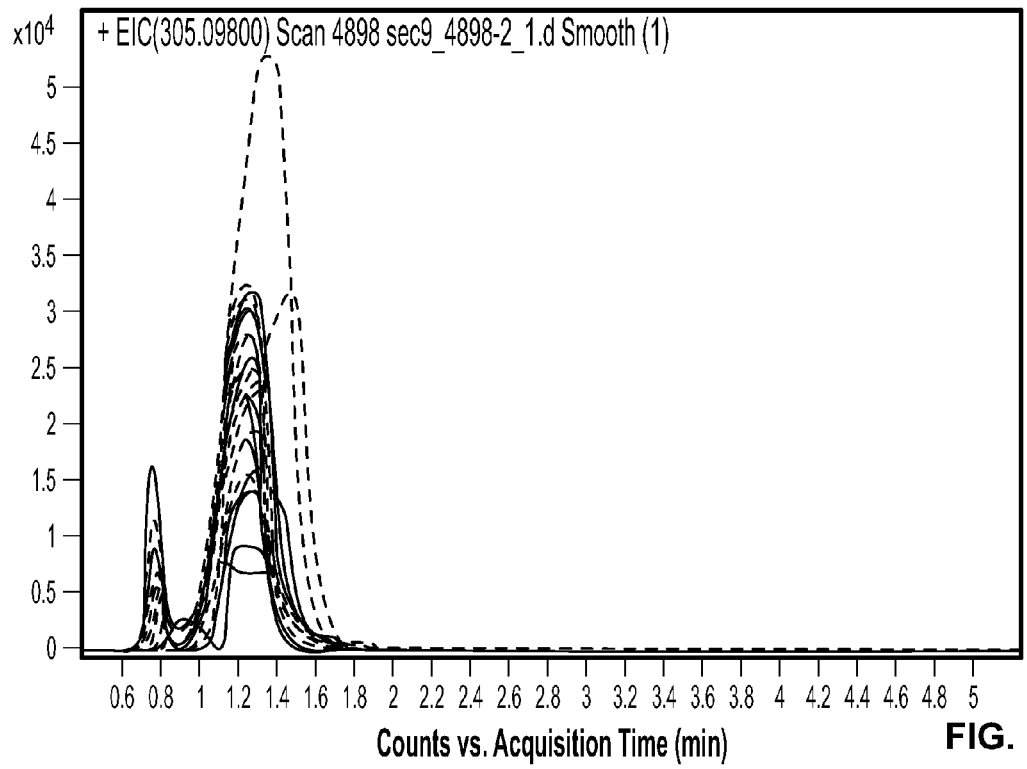
FIG. 6 (A)-FIG. 6 (C) are extracted ion chromatograms (EICs) of N-acetylaspartylglutamic acid (NAAG), and FIG. 6 (D) is a plot of the relative abundance of N-acetylaspartylglutamic acid in autistic and control brain samples.
Figure 6B:
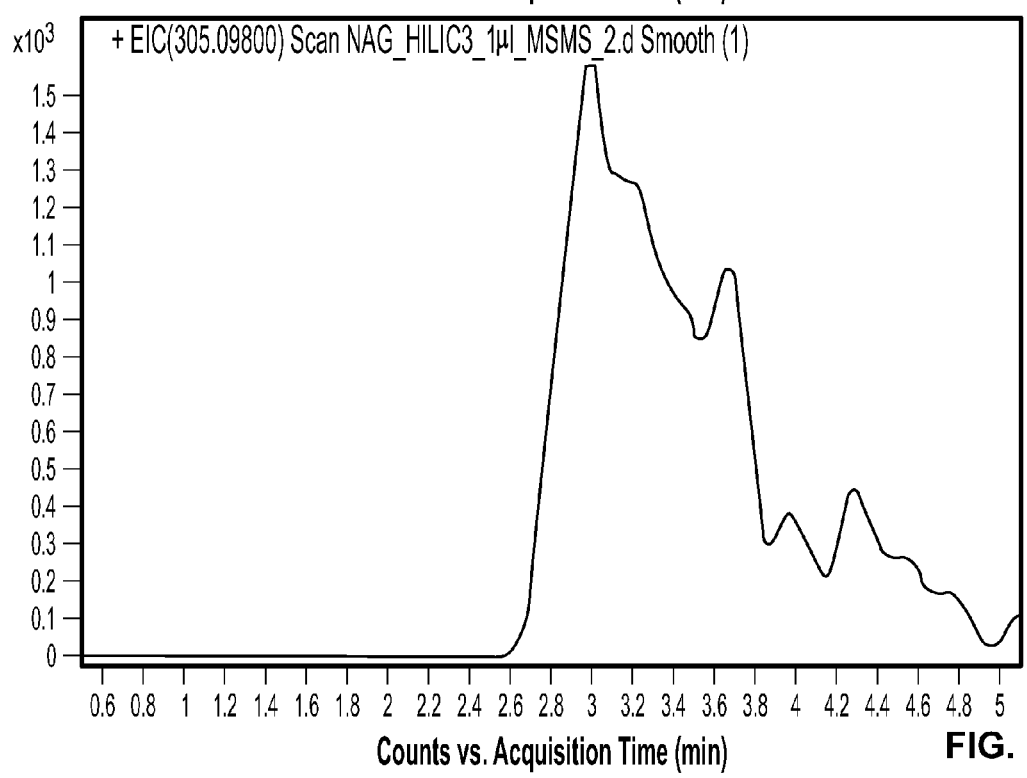
Figure 6C:
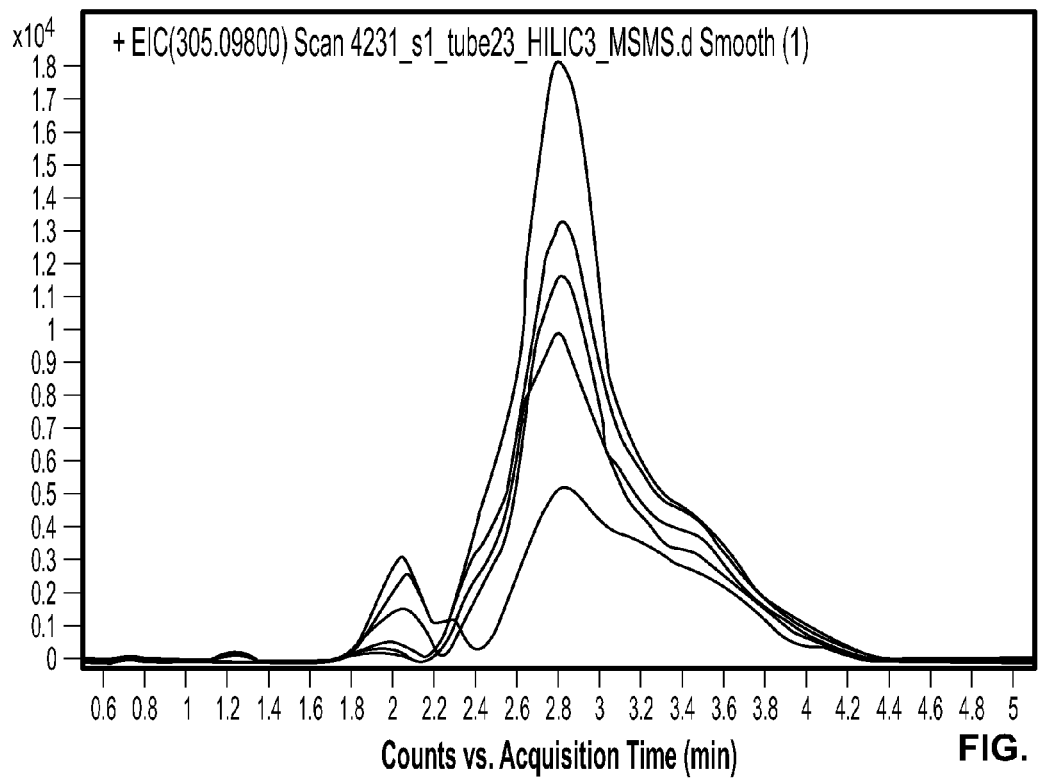
Figure 6D:
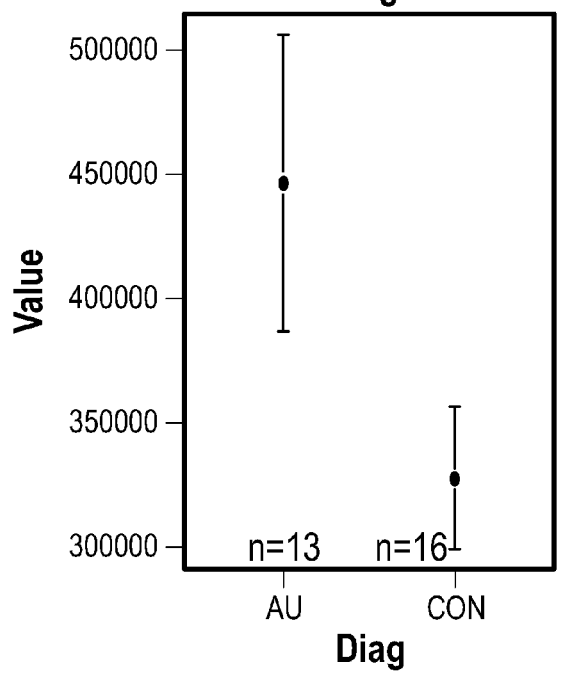

The abundance of N-acetylaspartylglutamic acid (exact mass 304.091) was elevated in post-mortem autistic brains in comparison to normal controls. These results are consistent with previously reported perturbations in the glutamate pathway for a human in vitro model of autism (Cezar et al., 2007, *Stem Cells Dev*. 16:869-882), as well as other clinical studies (Blaylock et al., 2009, *Curr. Med. Chem.* 16:157-170; Friedman et al., 2006, *Arch. Gen. Psychiatry*, 63:786-794; Kleinhans et al., 2007, *Brain Res.* 1162, 85-97; Pardo et al., 2007, *Brain Pathol.* 17:434-447; Shinohe et al., 2006, *Prog. Neuro-Psychopharmacol. Biol. Psychiatry*, 30:1472-1477). However, unlike previous reports, the results set forth herein show a previously unappreciated direct perturbation to the glutamate metabolism intermediate, N-acetylaspartylglutamic acid. Showing statistical significance (p=0.054, FIGS. 6(A) and 6(D)), the chemical identity of N-acetylaspartylglutamic acid was confirmed by comparative mass spectrometry, revealing both a retention time (FIGS. 6(B) and 6(C)) and ion fragmentation pattern between the postmortem brain samples (FIG. 4(C)) and the chemical standard (FIG. 4(D)).

Unspecified Compounds

Figure 7B:
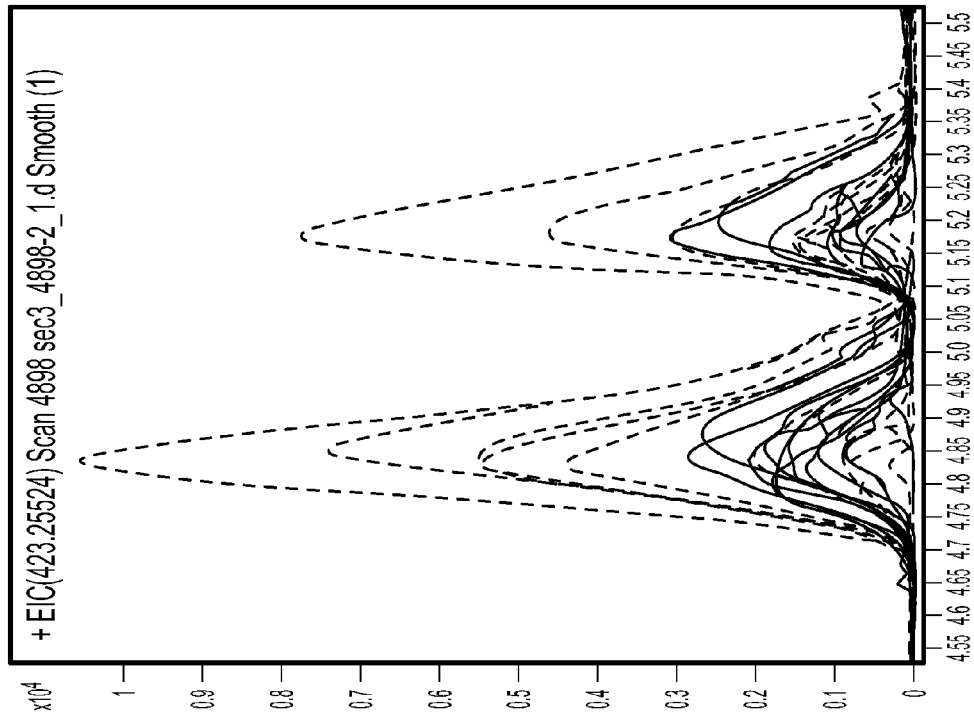
FIG. 7 (A) and FIG. 7 (B) are extracted ion chromatograms (EICs) of yet to be identified metabolites. Multiple unknown compounds were observed to be significantly different between autistic and control brain samples. The EICs of two such metabolites are shown for molecules with the exact mass of 366.1426 (FIG. 7 (A)) and 422.2482 (FIG. 7 (B)).
Figure 7A:
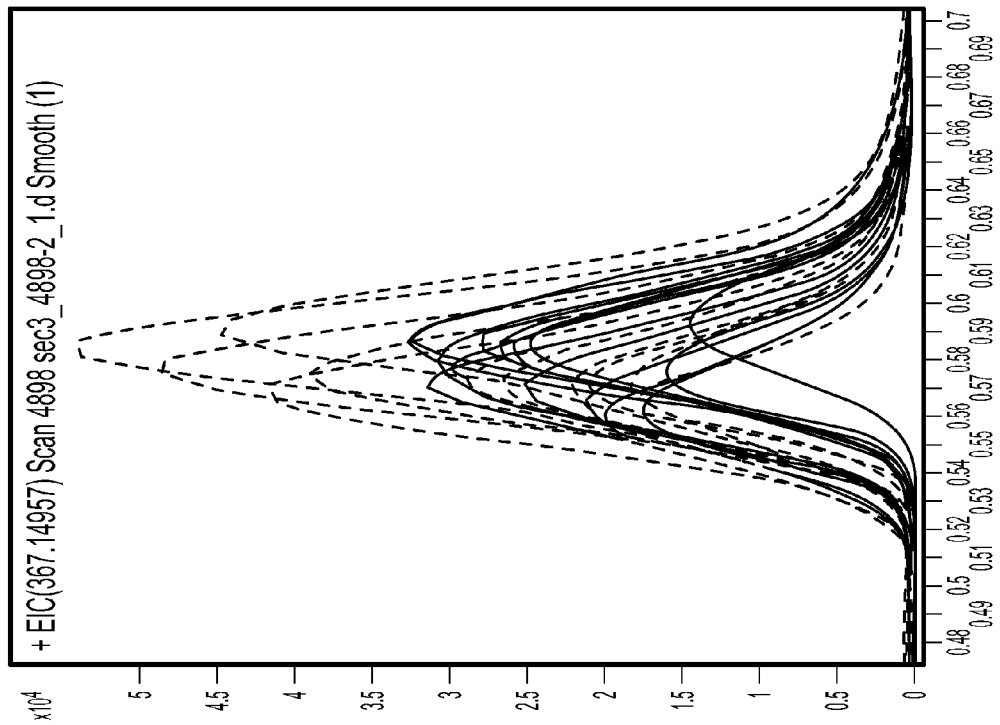

In addition to those metabolites described above, the metabolomics analyses described herein identified alterations in multiple non-annotated metabolites (i.e., not annotated in public databases). Abundance of these metabolites was significantly increased or decreased in autistic brain samples as compared to controls (p<0.05). The extracted ion chromatograms of two such unspecified small molecule metabolites are shown in FIGS. 7(A) and 7(B) (exact masses 366.1426 and 422.2482, respectively). Both of these non-annotated endogenous metabolites were significantly increased in autistic brain regions. Feature A (exact mass 366.1426) had a 42% increase in abundance between autistic and control brain samples. The abundance of feature B (exact mass 422.2482) was increased 181% in autistic brain samples. Lack of current annotation of these metabolites in public databases does not exclude them as candidate diagnostic biomarkers for autism. The highly sensitive, quantitative nature of the analytical chemistry detection system employed herein provides a measurable endpoint (i.e., exact mass), which can be measured in patient samples (e.g., tissues or biofluids) from autistic patients. In addition, other analytical platforms, sch as NMR, can be used to confirm the chemical formula of these compounds. An absence in chemical annotation merely prevents mapping of the molecules onto a specific biochemical pathway.

In summary, statistically significant differences were detected in the abundance of multiple metabolites ranging in size from about 10 to about 1500 Daltons between postmortem autistic and non-autistic brain samples (Table 2). HILIC chromatography followed by positive mode ESI-QTOF ionization identified a total of 98 metholites that were statistically significantly different (p<0.05) between autistic brain and non-autistic controls. Additionally, C18 chromatography followed by positive mode ESI-QTOF ionization, generated 47 statistically significant metabolites (p<0.05). This comprehensive signature provides immediate means for translational approaches to examine if perturbations to these endogenous chemicals are also measured in a quantitative manner in biofluids.

Example 4

Identification and Assessment of Metabolites Secreted in Patient Biofluids

While the assessment of brain tissue, the organ primarily affected by autism, permits the identification of autistic biomarkers as described herein, the inventive methods are not limited to the examination of brain tissue. Analyzing patient samples such as biofluids, including for example, cerebrospinal fluid, blood, plasma, amniotic fluid and urine, i.e., complex mixtures of extracellular biomolecules will also enable the identification and assessment of differentially secreted metabolites. This method is advantageous over invasive procedures such as tissue biopsies because small molecules present in biofluids can be detected non-invasively (in contrast to intracellular compounds). In addition, processing cellular supernatant for mass spectrometry is more robust and less laborious than cellular extracts. Cellular extracts from, for example, tissue biopsies or lysed cells, are encompassed in the methods of the invention.

Furthermore, one of skill would appreciate the secretion of brain metabolites into surrounding cerebrospinal fluid. In turn, the collection and assessment of cerebrospinal fluid by the described methods (i.e., metabolomics analysis) will permit the analysis and identification of differentially expressed metabolites. Using the methods of the current invention, specific analytical chemistry protocols can be used for assessing cerebrospinal fluid and other biofluids for defined exact mass and retention times of specific candidate biomarkers.

Thus, in these aspects of the inventive methods a biofluid is obtained, such as cerebrospinal fluid, using conventional techniques (e.g., lumbar puncture) and the biofluid processed as set forth herein to remove proteins and other biological materials having a molecular weight greater than about 3000 Daltons. Separation methods, for example LC-TOF mass spectrometry, are applied to the processes biofluid and metabolites detected therein. Detection of one or a plurality of differentially produced metabolites characteristic for autism is used to identify a subject having or at risk for autism, and to indicate that further behavioral and other diagnostic methods are indicated.

Similarly, one of skill would appreciate the secretion of brain small metabolites across the blood-brain barrier. Metabolomic analysis of blood plasma has been performed on blood samples obtained from mammals as described: Thaw plasma and add 450 ul of ice cold MeOH:$H_2O$ (8:1 v/v) and agitate for 10 minutes at 2-8 C. Then centrifuge the samples at 18,400×g for 20 minutes at 4 C and transfer the supernatant to a tube and repeat steps 3 and 4 until no pellet is observed. Dry samples and then re-solublize in 50 ul of 50:50 ACN: 0.1% formic acid for subsequent metabolic analysis. In summary, the inventive methods are applied to biofluids including cerebrospinal fluid and plasma as two examples.

Example 5

Identification of Biochemical and Metabolic Pathways Altered in Autistic Brain

Statistically significant metabolites whose chemical identity was confirmed as described above were compared and mapped in silico to the Kyoto Encyclopedia of Genes and Genomes (KEGG) pathway database. A Fisher's exact test was used find biochemical pathways that were statistically overrepresented. Groupings of features that show a common trend across samples also were evaluated using the KEGG database to determine if any biochemical interactions exist between the molecules that are not represented on a canonical KEGG pathway. This approach allowed mechanistic pathways that underlie metabolic changes observed in vivo to be identified. Mapping differential metabolomic profiles to their respective biochemical pathways as outlined in the Kyoto Encyclopedia of Genes and Genomes (KEGG, release 41.1, www.genome.jp/kegg) revealed specific metabolic pathways that were upregulated or downregulated in the cerebellum of autistic subjects in comparison to non-autistic controls. Significant changes to glutamate, cysteine, methionine, tryptophan and GABA metabolic pathways were detected in autistic brains in comparison to non-autistic controls.

The results of the metabolomic methods set forth herein measured simultaneous changes in multiple biochemical pathways and networks, providing a quantitative de facto biochemical signature of specific autistic brain regions. Comparative metabolomics between postmortem brains of autistic patients and non-autistic controls revealed robust biomarkers as well as biochemical changes that provide means for the early diagnosis of autism. The differentially secreted metabolites provided herein comprise several candidate diagnostic biomarkers for autism.

The invention is not intended to be limited to the disclosed embodiments of the invention. It should be understood that the foregoing disclosure emphasizes certain specific embodiments of the invention and that all modifications or alternatives equivalent thereto are within the spirit and scope of the invention as set forth in the appended claims.

What is claimed is:

1. A method of detecting levels of cellular metabolites in an individual suspected of having autism, the method comprising the steps of:
   (a) obtaining a biosample comprising brain tissue from an individual;
   (b) detecting levels of a plurality of cellular metabolites in the biosample using liquid chromatography electro spray-ionization time of flight mass spectrometry, wherein the cellular metabolites are selected from N-acetylaspartylglutamic acid, 2-aminooctanoic acid, 5-hydroxylysine, vinylacetylglycine, proline, betaine, 3-carboxy-1-hydroxypropylthiamine diphosphate, 3'-sialyllactosamine, 3,4-dihydroxybenzylamine, dipalmitoyl-phosphatidylcholine, and SAICAR ((S)-2-[5-Amino-1-(5-phospho-D-ribosyl) imidazole-4-carboxamido]succinate).

2. The method of claim 1 further comprising detecting levels of the plurality of cellular metabolites in a second biosample of brain tissue obtained from an individual without autism.

3. The method of claim 2, wherein the levels of the plurality of cellular metabolites in the second biosample are detected using liquid chromatography electro spray-ionization time of flight mass spectrometry.

4. A method of detecting levels of a plurality of cellular metabolites in a biosample, the method comprising the steps of:
   assaying a biosample comprising brain tissue isolated from a human patient suspected of having autism for levels of a plurality of cellular metabolites having a molecular weight of from about 10 Daltons to about 1500 Daltons: and
   detecting levels of the plurality of cellular metabolites in the biosample by liquid chromatography electro spray-ionization time of flight mass spectrometry;
   wherein the plurality of cellular metabolites comprises N-acetylaspartylglutamic acid, 2-aminooctanoic acid, 5-hydroxylysine, vinylacetylglycine, proline, betaine, 3-carboxy-1-hydroxypropylthiamine diphosphate, 3'-sialyllactosamine, 3,4-dihydroxybenzylamine, dipalmitoyl-phosphatidylcholine, and SAICAR ((S)-2-[5-Amino-1-(5-phospho-D-ribosyl) imidazole-4-carboxamido]succinate).

5. The method of claim 4 further comprising detecting levels of the plurality of cellular metabolites in a second biosample of brain tissue obtained from a human individual without autism.

6. The method of claim 5, wherein the levels of the plurality of cellular metabolites in the second biosample are detected using liquid chromatography electro spray-ionization time of flight mass spectrometry.

* * * * *